(12) United States Patent
Alexandrov

(10) Patent No.: US 10,925,925 B2
(45) Date of Patent: Feb. 23, 2021

(54) THERAPY OF ATHEROSCLEROSIS, PRIMARY BILIARY CIRRHOSIS AND NRLP3 INFLAMMASOME-ASSOCIATED DISEASE BY HTCP INHIBITORS

(71) Applicant: MYR GmbH, Burgwedel (DE)

(72) Inventor: Alexander Alexandrov, Bad Homburg (DE)

(73) Assignee: MYR GMBH, Burgwedel (DE)

( * ) Notice: Subject to any disclaimer, the term of this patent is extended or adjusted under 35 U.S.C. 154(b) by 47 days.

(21) Appl. No.: 15/951,850

(22) Filed: Apr. 12, 2018

(65) Prior Publication Data
US 2018/0296634 A1 Oct. 18, 2018

(30) Foreign Application Priority Data

Apr. 18, 2017 (EP) ..................................... 17166828

(51) Int. Cl.
| | | |
|---|---|---|
| A61P 1/16 | (2006.01) | |
| A61K 38/16 | (2006.01) | |
| A61K 45/06 | (2006.01) | |
| C07K 14/02 | (2006.01) | |

(52) U.S. Cl.
CPC ............ *A61K 38/162* (2013.01); *A61K 45/06* (2013.01); *A61P 1/16* (2018.01); *C07K 14/02* (2013.01); *A61K 2300/00* (2013.01); *C12N 2730/10122* (2013.01); *C12N 2730/10133* (2013.01); *C12N 2760/10122* (2013.01); *C12N 2760/10133* (2013.01)

(58) Field of Classification Search
CPC .. A61K 38/162; A61K 45/06; A61K 2300/00; C07K 14/02; C07K 14/005; A61P 1/16; A61P 3/10; A61P 25/28; A61P 9/10; C12N 2730/10122; C12N 2760/10122; C12N 2730/10133; C12N 2760/10133
See application file for complete search history.

(56) References Cited

U.S. PATENT DOCUMENTS

2011/0020397 A1* 1/2011 Mier .................... A61K 47/542
424/227.1

FOREIGN PATENT DOCUMENTS

WO 2016055534 A2 4/2016

OTHER PUBLICATIONS

Guo et al (Immunity, 2016, 45, 802-816) (Year: 2016).*
Watashi et al (Int.J.Mol.Sci., 2014, 15, 2892-2905) (Year: 2014).*
Haag et al (Anal Bioanal Chem, 2015, 407, 6815-6825) (Year: 2015).*
Blank et al (Journal of Hepatology, 2016, 65, 483-489) (Year: 2016).*
Lempp F.A., et al., "Inhibitors of Hepatitis B Virus Attachment and Entry", Intervirology, 2014, vol. 57, No. 3-4, pp. 151-157.
Eirini I Rigopoulou, et al., "Primary biliary cirrhosis in HBV and HCV patients: Clinical characteristics and outcome", World J Hepatol., 2013, 5(10): 577-583.
Oehler N. et al., "Binding of hepatitis B virus to its cellular receptor alters the expression profile of genes of bile acid metabolism", Hepatology, 2014, 60(5):1483-1493.
Search Report issued for European Patent Application No. 17 16 6828 dated Aug. 2, 2017 (8 pages).

* cited by examiner

*Primary Examiner* — Sudhakar Katakam
(74) *Attorney, Agent, or Firm* — Rothwell, Figg, Ernst & Manbeck, P.C.

(57) ABSTRACT

An inhibitor of Na+-taurocholate cotransporting polypeptide (NTCP) for use in a method of treatment of primary biliary cirrhosis, atherosclerosis, or an NRLP3 inflammasome-associated disease in a subject.

18 Claims, 3 Drawing Sheets
Specification includes a Sequence Listing.

SEQUENCE LISTING

<160> NUMBER OF SEQ ID NOS: 20

<210> SEQ ID NO 1

-continued

```
<211> LENGTH: 59
<212> TYPE: PRT
<213> ORGANISM: Artificial Sequence
<220> FEATURE:
<223> OTHER INFORMATION: HBV preS1 consensus sequence (positions (-11)
      to 48)

<400> SEQUENCE: 1

Met Gly Gly Trp Ser Ser Thr Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Arg Ala Asn Ser Asn Asn Pro Asp Trp Asp Phe Asn Pro Asn
        35                  40                  45

Lys Asp His Trp Pro Glu Ala Asn Lys Val Gly
    50                  55

<210> SEQ ID NO 2
<211> LENGTH: 59
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly
    50                  55

<210> SEQ ID NO 3
<211> LENGTH: 59
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala Asn Lys Val Gly
    50                  55

<210> SEQ ID NO 4
<211> LENGTH: 59
<212> TYPE: PRT
<213> ORGANISM: Hepatitis B virus

<400> SEQUENCE: 4

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly
```

```
                50                  55

<210> SEQ ID NO 5
<211> LENGTH: 48
<212> TYPE: PRT
<213> ORGANISM: Hepatitis B virus

<400> SEQUENCE: 5

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

<210> SEQ ID NO 6
<211> LENGTH: 58
<212> TYPE: PRT
<213> ORGANISM: Hepatitis B virus

<400> SEQUENCE: 6

Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly
    50                  55

<210> SEQ ID NO 7
<211> LENGTH: 59
<212> TYPE: PRT
<213> ORGANISM: Hepatitis B virus

<400> SEQUENCE: 7

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly
    50                  55

<210> SEQ ID NO 8
<211> LENGTH: 58
<212> TYPE: PRT
<213> ORGANISM: Hepatitis B virus

<400> SEQUENCE: 8

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly
    50                  55
```

<210> SEQ ID NO 9
<211> LENGTH: 59
<212> TYPE: PRT
<213> ORGANISM: Hepatitis B virus

<400> SEQUENCE: 9

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly
    50                  55

<210> SEQ ID NO 10
<211> LENGTH: 48
<212> TYPE: PRT
<213> ORGANISM: Wooly Monkey Hepatitis B virus

<400> SEQUENCE: 10

Met Gly Leu Asn Gln Ser Thr Phe Asn Pro Leu Gly Phe Phe Pro Ser
1               5                   10                  15

His Gln Leu Asp Pro Leu Phe Lys Ala Asn Ala Gly Ser Ala Asp Trp
            20                  25                  30

Asp Lys Asn Pro Asn Lys Asp Pro Trp Pro Gln Ala His Asp Thr Ala
        35                  40                  45

<210> SEQ ID NO 11
<211> LENGTH: 59
<212> TYPE: PRT
<213> ORGANISM: Artificial Sequence
<220> FEATURE:
<223> OTHER INFORMATION: HBV preS1 Genotype C (positions (-11) to 48)
      with amino acid substitution at position 46 (Gln/Q -> Lys/K)

<400> SEQUENCE: 11

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Lys Val Gly
    50                  55

<210> SEQ ID NO 12
<211> LENGTH: 47
<212> TYPE: PRT
<213> ORGANISM: Artificial Sequence
<220> FEATURE:
<223> OTHER INFORMATION: HBV preS1 consensus sequence (positions 2 to
      48)

<400> SEQUENCE: 12

Gly Thr Asn Leu Ser Val Pro Asn Pro Leu Gly Phe Phe Pro Asp His
1               5                   10                  15

Gln Leu Asp Pro Ala Phe Arg Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: HBV preS1 Genotype C (positions 2 to 48) with
      amino acid substitution at position 46 (Gln/Q -> Lys/K)

<400> SEQUENCE: 13

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 14
<211> LENGTH: 47
<212> TYPE: PRT
<213> ORGANISM: Hepatitis B virus

<400> SEQUENCE: 14

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 15
<211> LENGTH: 7
<212> TYPE: PRT
<213> ORGANISM: Artificial Sequence
<220> FEATURE:
<223> OTHER INFORMATION: synthesized pre-S1 peptide inhibitor
<220> FEATURE:
<221> NAME/KEY: Xaa
<222> LOCATION: (6)..(6)
<223> OTHER INFORMATION: Xaa is any amino acid, preferably Phe or Leu,
      more preferably Phe

<400> SEQUENCE: 15

Asn Pro Leu Gly Phe Xaa Pro
1               5

<210> SEQ ID NO 16
<211> LENGTH: 5
<212> TYPE: PRT
<213> ORGANISM: Artificial Sequence
<220> FEATURE:
<223> OTHER INFORMATION: synthesized pre-S1 peptide inhibitor
<220> FEATURE:
<221> NAME/KEY: Xaa
<222> LOCATION: (2)..(2)
<223> OTHER INFORMATION: Xaa is any amino acid
<220> FEATURE:
<221> NAME/KEY: Xaa
<222> LOCATION: (4)..(4)
<223> OTHER INFORMATION: Xaa is any amino acid
<220> FEATURE:
<221> NAME/KEY: Xaa
<222> LOCATION: (5)..(5)
<223> OTHER INFORMATION: Xaa is any amino acid

<400> SEQUENCE: 16

Asn Xaa Ser Xaa Xaa

```
<210> SEQ ID NO 17
<211> LENGTH: 12
<212> TYPE: PRT
<213> ORGANISM: Artificial Sequence
<220> FEATURE:
<223> OTHER INFORMATION: synthesized pre-S1 peptide inhibitor
<220> FEATURE:
<221> NAME/KEY: Xaa
<222> LOCATION: (2)..(2)
<223> OTHER INFORMATION: Xaa is Leu, Ile or Gln, preferably Leu
<220> FEATURE:
<221> NAME/KEY: Xaa
<222> LOCATION: (4)..(4)
<223> OTHER INFORMATION: Xaa is Thr, Val, Ala or is absent, preverably
      Thr or Val, more preferably Thr
<220> FEATURE:
<221> NAME/KEY: Xaa
<222> LOCATION: (5)..(5)
<223> OTHER INFORMATION: Xaa is Pro, Ser, Thr or Phe, preverably Pro or
      Ser, more preferably Ser
<220> FEATURE:
<221> NAME/KEY: Xaa
<222> LOCATION: (5)..(5)
<223> OTHER INFORMATION: Xaa is Pro, Ser, Thr or Phe, preferably Pro or
      Ser, more preferably Ser
<220> FEATURE:
<221> NAME/KEY: Xaa
<222> LOCATION: (11)..(11)
<223> OTHER INFORMATION: Xaa is any amino acid

<400> SEQUENCE: 17

Asn Xaa Ser Xaa Xaa Asn Pro Leu Gly Phe Xaa Pro
1               5                   10

<210> SEQ ID NO 18
<211> LENGTH: 6
<212> TYPE: PRT
<213> ORGANISM: Artificial Sequence
<220> FEATURE:
<223> OTHER INFORMATION: synthesized
<220> FEATURE:
<221> NAME/KEY: Xaa
<222> LOCATION: (1)..(1)
<223> OTHER INFORMATION: Xaa is any amino acid or preferred Asp, Glu or
      Ser, preferably Asp or Glu, more preferably Asp

<400> SEQUENCE: 18

Xaa His Gln Leu Asp Pro
1               5

<210> SEQ ID NO 19
<211> LENGTH: 13
<212> TYPE: PRT
<213> ORGANISM: Artificial Sequence
<220> FEATURE:
<223> OTHER INFORMATION: synthesized
<220> FEATURE:
<221> NAME/KEY: Xaa
<222> LOCATION: (6)..(6)
<223> OTHER INFORMATION: Xaa is any amino acid
<220> FEATURE:
<221> NAME/KEY: Xaa
<222> LOCATION: (8)..(8)
<223> OTHER INFORMATION: Xaa is Asp, Glu or Ser, preferably Asp or Glu,
      more preferably Asp

<400> SEQUENCE: 19

Asn Pro Leu Gly Phe Xaa Pro Xaa His Gln Leu Asp Pro
1               5                   10
```

```
<210> SEQ ID NO 20
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: Xaa
<222> LOCATION: (2)..(2)
<223> OTHER INFORMATION: Xaa is Leu, Ile or Gln, preferably Leu
<220> FEATURE:
<221> NAME/KEY: Xaa
<222> LOCATION: (4)..(4)
<223> OTHER INFORMATION: Xaa is Thr, Val, Ala or is absent, preverably
      Thr or Val, more preferably Thr
<220> FEATURE:
<221> NAME/KEY: Xaa
<222> LOCATION: (5)..(5)
<223> OTHER INFORMATION: Xaa is Pro, Ser, Thr or Phe, preverably Pro or
      Ser, more preferably Ser
<220> FEATURE:
<221> NAME/KEY: Xaa
<222> LOCATION: (11)..(11)
<223> OTHER INFORMATION: Xaa is any amino acid
<220> FEATURE:
<221> NAME/KEY: Xaa
<222> LOCATION: (13)..(13)
<223> OTHER INFORMATION: Xaa is Asp, Glu or Ser, preverably Asp or Glu,
      more preferably Asp

<400> SEQUENCE: 20

Asn Xaa Ser Xaa Xaa Asn Pro Leu Gly Phe Xaa Pro Xaa His Gln Leu
1               5                   10                  15

Asp Pro
```

THERAPY OF ATHEROSCLEROSIS, PRIMARY BILIARY CIRRHOSIS AND NRLP3 INFLAMMASOME-ASSOCIATED DISEASE BY HTCP INHIBITORS

CROSS REFERENCE TO RELATED APPLICATION

This application claims the priority to European Application Number 17 166 828.8 filed Apr. 18, 2017, the disclosure of which is incorporated herein in its entirety by reference.

The present application includes a Sequence Listing filed in electronic format. The Sequence Listing is entitled "2185-371_ST25.txt" created on Jun. 27, 2018, and is 12,000 bytes in size. The information in the electronic format of the Sequence Listing is part of the present application and is incorporated herein by reference in its entirety.

FIELD OF INVENTION

The present invention pertains to novel therapy of atherosclerosis, primary biliary cirrhosis, or an NRLP3 inflammasome-associated disease. In particular, the invention provides NTCP inhibitors, preferably pre-S1 peptide inhibitors, and compositions comprising same, for the treatment of said diseases. Method of treatment of said diseases by NTCP inhibitors, preferably pre-S1 peptide inhibitors, are also provided.

BACKGROUND OF THE INVENTION

Atherosclerosis

Atherosclerosis, also known as arteriosclerotic vascular disease or ASVD is a disease associated with invasion and accumulation of white blood cells especially macrophages and subsequent proliferation of intima and appearance of plaques.

Atherosclerosis is initiated by the accumulation of low-density lipoprotein (LDL) in the intima of the artery, and elevated LDL cholesterol is the leading risk factor for cardiovascular disease. The HMGCoA reductase inhibitors (statins) have been widely used to lower plasma LDL cholesterol level and reduce the incidence of major vascular events and cardiovascular death. In addition to statins, research over the past several decades has led to the development of a number of drugs that influence cholesterol homeostasis. For example, ezetimibe inhibits the action of Niemann-Pick C1-like 1 (NPC1L 1), a protein on the intestinal brush border membrane that plays an important role in cholesterol absorption. Bile acid sequestrants inhibit cholesterol absorption, as well as bile acid reabsorption. High-density lipoprotein (HDL) cholesterol levels, on the other hand, are inversely correlated with disease risk, and HDL mediates reverse cholesterol transport and exhibits antioxidative activities. Drug therapies that attempted to raise HDL cholesterol level or improve HDL functions have been investigated, but so far with limited success (Shih et al., 2013).

Despite the availability of treatment options, major unmet medical need exists in the treatment of atherosclerosis. Especially, the reduction of existing plaque burden in patients with advanced symptomatic atherosclerosis is an unresolved issue.

Primary Biliary Cirrhosis

Primary biliary cirrhosis, also known as primary biliary cholangitis (PBC), is a chronic cholestatic liver disease of unknown cause. Progressive bile-duct injury from portal and periportal inflammation could result in progressive fibrosis and eventual cirrhosis. Evidence to date suggests that immunological and genetic factors play a role in the disease. Affected individuals are typically middle-aged women with asymptomatic rises of serum hepatic biochemical variables. Fatigue, pruritus, or unexplained hyperlipidaemia at initial presentation might also suggest a diagnosis of primary biliary cirrhosis.

Present evidence supports to the notion of primary biliary cirrhosis being an immune-mediated disease. Cellular and humoral abnormalities have both been noted. Immunohistochemical staining of T lymphocytes in portal and periportal areas shows CD4-positive and CD8-positive T cells. Furthermore, abnormal suppressor T-cell activity has been reported in asymptomatic first-degree relatives of affected individuals. Intracellular adhesion molecules (e.g., ICAM-1), which are expressed in areas of epithelial-cell damage, may also participate in pathogenesis of primary biliary cirrhosis (Talwalkar & Lindor, 2003). It has also been observed that interleukin-1β (IL-1β) may play a role in the pathogenesis of PBC by contributing to altered immune function and fibrosis (Mueller et al, 1995).

The only approved current treatment option for PBC are bile acid therapies with ursodeoxicholic acid (UDSA) and obeticholic acide (OCA). The mechanism of action of both drugs in PBC is linked to their ability to activate FXR and TGFR-5, thus leading to exertion of anti-inflammatory effects. UDCA was approved by FDA for treatment of PBC in 1997. However, about 40% of patient treated with UDCA do not achieve adequate biochemical response.

For a recently approved OCA, 90% of patients enrolled in the pivotal trial had early stage PBC with normal total bilirubin (TB) and normal albumin levels at baseline, whereas the majority of patients included into the study have received treatment with UDCA. Although the primary endpoint was pre-specified as a reduction in both alkalic phosphatase (ALP) and TB, due to the nature of the enrollment population, the primary endpoint was driven by ALP alone. In the phase 3 clinical trial at month 12, a total of 46% patients in OCA titration arm and 47% patients in the OCA 10 mg arm achieved the primary endpoint (predominantly due to reduction in ALP), compared to 10% patients in the placebo arm.

Therefore, a significant medical need exists in the treatment of PBC, especially for patients with advanced disease.

NRLP3 Inlfammasome-Associated Diseases and NASH

The inflammasome is a cytosolic multimeric protein complex composed of nucleotide-binding domain and leucine-rich repeat-containing proteins (NLRs) or AIM2, adaptor protein ASC, and caspase-1. It plays a key role in host defense against pathogens and inflammation (Davis et al., 2011; Martinon et al., 2006). Activation of the inflammasome is involved in the pathogenesis of several inflammatory disorders, including type-2 diabetes, atherosclerosis, gout, and Alzheimer's disease. In particular, accumulated data strongly indicate that type-2 diabetes is an inflammatory disease. The chronic caloric excess-driven influx of macrophages as well as other immune cells and the subsequent amplified pro-inflammatory milieu play key roles in the B-cell disfunction and insulin resistance. Clinically, elevated circulating IL-1β is a risk factor for the development of type-2 diabetes in humans. Mouse models and human clinical trials suggest that antagonism of IL-1β might be a promising treatment for type-2 diabetes (Schroder, et al., 2010; Guo et al., 2016).

It is well known that bile acids bind and activate several nuclear receptors, including the farnesoid X receptor (FXR).

FXR is highly expressed in the liver and intestine, regulating the transcription of specific target genes involved in the bile acid, lipid, and glucose metabolism. Recent studies revealed that bile acids also serve as ligands for the G-protein-coupled receptor, TGR5 (or the G-protein-coupled bile acid receptor-1). TGR5 is expressed in various tissues and cell types, with relatively high expression in the gall bladder, intestine, placenta, and spleen. Previous in vitro studies showed that activation of TGR5 suppresses proinflammatory cytokine production and phagocytosis of monocytes/macrophages. In vivo studies indicated that the immunosuppressive properties of TGR5 also include protective role in metabolic diseases, such as atherosclerosis and diabetes mellitus, in which tissue infiltration and activation of immune cells is a hallmark of their initiation and development. Anti-inflammatory and anti-fibrotic properties of FXR and TGR5 signaling can be successfully used in the treatment of nonalcoholic steatohepatitis (NASH).

SUMMARY OF THE INVENTION

The invention provides an NTCP inhibitor for use in a method of treatment of primary biliary cirrhosis (PBC) in a subject. Also provided is a method of treatment of primary biliary cirrhosis in a subject by providing to the subject in need thereof an effective amount of an NTCP inhibitor. It is envisaged that administration of an NTCP inhibitor leads to an improvement of primary biliary cirrhosis, including normalization of biochemical parameters and decrease in inflammation and fibrosis progression. An NTCP inhibitor for use according to the invention may be administered to the subject individually or together and/or in combination with other medication for the treatment of primary biliary cirrhosis.

The invention further provides an NTCP inhibitor for use in a method of treatment of atherosclerosis, in a subject. Also provided is a method of treatment of atherosclerosis in a subject by providing to the subject in need thereof an effective amount of an NTCP inhibitor. It is envisaged that administration of an NTCP inhibitor leads to an improvement of atherosclerotic condition, including decrease, resorption or elimination of atherosclerotic plaques. An NTCP inhibitor for use according to the invention may be administered to the subject individually or together, and/or in combination with other medication for the treatment of atherosclerosis.

The invention further provides an NTCP inhibitor for use in a method of treatment of other NRLP3 inflammasome-associated diseases in a subject. Specifically, treatment of type-2 diabetes, atherosclerosis, gout, Alzheimer's disease and NASH is provided. Also provided is a method of treatment of and NRLP3 inflammasome-associated diseases, as defined above, in a subject by providing to the subject in need thereof an effective amount of an NTCP inhibitor. It is envisaged that administration of an NTCP inhibitor leads to an improvement of and NRLP3 inlfammasome-associated diseases, including normalization of biochemical parameters and improvement of disease progression. An NTCP inhibitor for use according to the invention may be administered to the subject individually or together and/or in combination with other medication for the treatment of and NRLP3 inflammasome-associated diseases.

In one aspect, the NTCP inhibitor of the invention may be a pre-S1 peptide inhibitor, wherein the pre-S1 peptide inhibitor comprises a peptide comprising amino acid sequence NPLGFX$_0$P (SEQ ID NO: 15), and wherein X$_0$ is any amino acid, preferably F or L, more preferably F. The pre-S1 peptide inhibitor may further comprise an N-terminal sequence of at least 4 amino acids at the N-terminus of NPLGFX$_0$P (SEQ ID NO: 15). The N-terminal sequence can be of any length above 4 amino acids, but preferably not longer than 19 amino acids. It is preferred that at least one amino acid of the N-terminal sequence has an amino group in a side chain. Thus, the pre-S1 peptide inhibitor may comprise amino acid sequence NX$_1$SX$_2$X$_3$ (SEQ ID NO: 16), wherein X$_1$, X$_2$ and X$_3$ is any amino acid, at the N-terminus, preferably directly attached to NPLGFX$_0$P (SEQ ID NO: 15). It is preferred that X$_1$ is L, I or Q, preferably L; X$_2$ is T, V, A or is absent, preferably T or V, more preferably T; and/or X$_3$ of is P, S, T or F, preferably P or S, more preferably S. Thus, the pre-S1 peptide inhibitor may comprise amino acid sequence NX$_1$SX$_2$X$_3$NPLGFX$_0$P (SEQ ID NO: 17), wherein X$_0$ is any amino acid; X$_1$ is L, I or Q, preferably L; X$_2$ is T, V, A or is absent, preferably T or V, more preferably T; and X$_3$ of is P, S, T or F, preferably P or S, more preferably S.

The pre-S1 peptide inhibitor may further comprise a C-terminal sequence of at least 1 amino acids at the N-terminus of NPLGFX$_0$P (SEQ ID NO: 15). The C-terminal sequence may be of any length, preferably not longer than 93 amino acids, no longer than 35 amino acids, no longer than 20 amino acids, or no longer than 10 amino acids. The pre-51 peptide inhibitor may comprise a C-terminal amino acid sequence X$_4$HQLDP (SEQ ID NO: 18), wherein X$_4$ is any amino acid. It is preferred that X$_4$ is D, E or S, preferably D or E, more preferably D. The C-terminal sequence is preferably directly attached to NPLGFX$_0$P (SEQ ID NO: 15). Accordingly, the pre-S1 peptide inhibitor may comprise amino acid sequence NPLGFX$_0$PX$_4$HQLDP (SEQ ID NO: 19), wherein X$_0$ is any amino acid; and X$_4$ is D, E or S, preferably D or E, more preferably D.

The pre-S1 peptide inhibitor may comprise amino acid sequence NX$_1$SX$_2$X$_3$NPLGFX$_0$PX$_4$HQLDP (SEQ ID NO: 20), wherein X$_0$ is any amino acid; X$_1$ is L, I or Q, preferably L; X$_2$ is T, V, A or is absent, preferably T or V, more preferably T; X$_3$ of is P, S, T or F, preferably P or S, more preferably S; and X$_4$ is D, E or S, preferably D or E, more preferably D.

The pre-S1 peptide inhibitor may be of any length of between 7 and 119 amino acids, 15 and 47 amino acids, or 15 and 25 amino acids. The pre-S1 peptide inhibitor may be 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 74, 80, 85, 90, 95, 100, 110, etc amino acids long.

The amino acid sequence NPLGFX$_0$P (SEQ ID NO: 15) comprised in the pre-S1 peptide inhibitor corresponds to amino acid position 9 to 15 of pre-S1 peptide of an HBV virus, according to standard preS peptide numbering. The above amino acid sequences NX$_1$SX$_2$X$_3$ (SEQ ID NO: 16) and X$_4$HQLDP (SEQ ID NO: 18) are correspond to amino acid position 4 to 8 and 16 to 21, respectively, of pre-S1 peptide of an HBV virus.

Thus, the pre-S1 peptide inhibitor may comprise a pre-S1 peptide of an HBV virus, or a functional fragment thereof. The functionality of the fragment may be assessed, e.g., based on its ability to bind to NTCP, inhibit NTCP, or reduce NTCP activity.

The pre-S1 peptide inhibitor may comprise at least amino acids 9 to 15 of a pre-S1 peptide of an HBV virus, according to standard preS peptide numbering. Alternatively, the pre-S1 peptide inhibitor may further comprise amino acids 4 to 8, 3 to 8, 2 to 8 of a pre-S1 peptide, and/or amino acids 16, 16 to 17, 16 to 18, 16 to 19, 16 to 19, 16 to 20, or 16 to of a pre-S1 peptide of an HBV virus. The pre-S1 peptide inhibitor may comprise or consist of amino acids 2 to 48 or 2 to 21 of a pre-S1 peptide of an HBV virus. Also contemplated are re-S1 peptide inhibitors with sequence identify of at least 50%, 55%, 60%, 65%, 70%, 75%, 80%, 85%, 90%, or 95% identity with any of the above sequences.

The HBV virus may be any HBV virus, e.g., HBV strain alphal, HBV strain LSH, woodchuck HBV, Woolly Monkey HBV (WMHBV), orangutan HBV, chimpanzee HBV, gorilla HBV, human HBV, HBV subtype AD, ADR, ADW, ADYW, AR or AYW, or HBV genotype A, B, C, D, E, F, G or H.

Exemplary pre-S1 peptide inhibitor comprises the amino acid sequence between positions 2 and 48 of the HBV pre-S1 consensus sequence:

```
                                         (SEQ ID NO: 12)
GTNL SVPNP LGFFP DHQLD PAFRA NSNNP DWDFN PNKDH
WPEAN KVG,
``` or between positions 2 and 48 of the HBV pre-S1 Genotype C sequence:

```
                                         (SEQ ID NO: 14)
GTNL SVPNP LGFFP DHQLD PAFGA NSNNP DWDFN PNKDH
WPEAN QVG,
``` or between positions 2 and 48 of the HBV pre-S1 Genotype C sequence with an amino acid substitution at position 46 (Gln (Q)→Lys (K)):

```
                                         (SEQ ID NO: 13)
GTNL SVPNP LGFFP DHQLD PAFGA NSNNP DWDFN PNKDH
WPEAN KVG,
``` or between positions 2 and 48 of the HBV pre-S1 Genotype D sequence:

```
                                         (SEQ ID NO: 5)
GQNL STSNP LGFFP DHQLD PAFRA NTANP DWDFN PNKDT
WPDAN KVG.
```

Also contemplated are fragments of the above amino acid sequences of at least 15 amino acids in length, as well as sequences having at least 50%, 55%, 60%, 65%, 70%, 75%, 80%, 85%, 90%, or 95% identity with any of the above exemplary sequences, wherein the activity of pre-S1 peptide inhibitor is maintained. The activity includes any of NTCP binding, NTCP inhibition, reduction of NTCP activity. The activity may also be prevention or reduction of HBV binding to NTCP.

The pre-S1 peptide inhibitor may be modified by one or more hydrophobic moieties at or around the N-terminus. The hydrophobic moiety modification may be by acylation, e.g., acylation with myristoyl or stearoyl.

A preferred pre-S1 peptide inhibitor has the amino acid sequence of

```
                                         (SEQ ID NO: 13)
GTNL SVPNP LGFFP DHQLD PAFGA NSNNP DWDFN PNKDH
WPEAN KVG,
``` wherein the peptide is modified at the N-terminus by myristoyl.

A preferred pre-S1 peptide inhibitor is Myrcludex B having the following chemical formula:

N-Myristoyl-glycyl-L-threonyl-L-asparaginyl-L-leucyl-L-seryl-L-valyl-L-prolyl-L-asparaginyl-L-prolyl-L-leucyl-glycyl-L-phenylalanyl-L-phenylalanyl-L-prolyl-L-aspartyl-L-histidyl-L-glutaminyl-L-leucyl-L-aspartyl-L-prolyl-L-alanyl-L-phenylalanyl -glycyl-L-alanyl-L-asparaginyl-L-seryl-L-asparaginyl-L-asparaginyl-L-prolyl-L-aspartyl-L-tryptophanyl-L-aspartyl-L-phenylalanyl-L -asparaginyl-L-prolyl-L-asparaginyl-L-lysyl-L-aspartyl-L-histidyl-L -tryptophanyl-L-prolyl-L-glutamyl-L-alanyl-L-asparaginyl-L-lysyl-L-valyl-glycinamide, acetate salt.

The pre-S1 peptide inhibitor may further be modified at the C-terminus or elsewhere to protect the peptide form degradation. Exemplary protective moieties that can be used for this purpose are D-amino acids, cyclic amino acids, modified amino acids, glycans, natural or synthetic polymers such as polyethylene glycol (PEG).

The pre-S1 peptide inhibitor of the invention, in particular Myrcludex B, may be administered to a patient at a dose such that the concentration of the pre-S1 peptide inhibitor at the NTCP site, i.e., in hepatocytes, is equal or above a Ki of about 1 to 10 nM. Thus a daily dose of the pre-S1 peptide inhibitor may be between 0.1 mg and 50 mg, 0.5 mg and 20 mg, 1 mg to 15 mg, 1 mg to 10 mg, 1 mg to 5 mg, for example 1 mg, 2 mg, 3 mg, 4, mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg, preferably 2 mg, 5 mg, or 10 mg, most preferably 5 mg. A daily dose of the pre-S1 peptide inhibitor may also be between about 0.0014 mg/kg body weight and about 0.7 mg/kg body weight, preferably between about 0.014 mg/kg body weight to about 0.28 mg/kg body weight (1 mg to 20 mg).

The pre-S1 peptide inhibitor may be administered for 2 weeks, 3, weeks, 4 weeks, 5 weeks, 6 weeks, 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3 years, or 4 years or longer.

The pre-S1 peptide inhibitor may be administered by any suitable rout such as subcutaneously, intravenously, orally, nasally, intramuscularly, transdermally, by inhalation or suppository, preferably intravenously or subcutaneously.

In another aspect, an NTCP inhibitor may be a compound or agent other than a pre-S1 peptide inhibitor that prevents or reduces production and/or function of NTCP.

NTCP inhibitors of the invention may be administered individually or together. In particular, the pre-S1 peptide inhibitor described above may be administered together with another NTCP inhibitor. The two of more NTCP inhibitors may be administered concurrently/concomitantly. According to this administration schedule, the administration of the two or more NTCP inhibitors timely overlaps. The duration of the administration of the two or more NTCP inhibitors may be identical or essentially identical. For example, a pre-S1 peptide inhibitor and another NTCP inhibitor may be administered for at least one cycle, or a course comprising one or more cycles (such as 2, 3, 4, 5, 6, 7, 8, 9 or 10 cycles). The duration of one cycle may be 1, 2, 3, 4, 5, 6, 7, 8, 9, 10, 11, or 12 weeks or longer. The duration of one cycle may be at least 1, 2, 3, 4, 5, 6, 7, 8, 9, 10, 11, or 12 weeks. The duration of one course may be 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3.0 years, or 4.0 years. For example, a 24 weeks course of pre-S1 peptide inhibitor Myrcludes B may be administered at the same time as a 24 weeks course of another NTCP inhibitor. In this administration scheme, Myrcludex B may be administered daily, whereas another NTCP inhibitor may be administered weekly. In this administration schedule, the pre-S1 peptide inhibitor and another NTCP inhibitor may be administered simultaneously, for example at essentially the same time or in a single composition.

The pre-S1 peptide inhibitor and a further NTCP inhibitor may be administered to the subject by various delivery routes, depending on the type of ingredient. Administration routs include enteral route (e.g., oraly and rectaly), parenteral route (e.g. intravenously, intramuscularly, subcutaneously, intraperitonealy), topically. Preferably, the pre-S1 peptide inhibitor is delivered subcutaneously.

The NTCP inhibitors for use according to the invention may be in a pharmaceutical composition comprising pharmaceutically acceptable carriers, excipients, adjuvants.

The invention is primarily intended for human treatment; however, treatment of any mammal is also included.

DETAILED DESCRIPTION OF THE INVENTION

Figure 1:
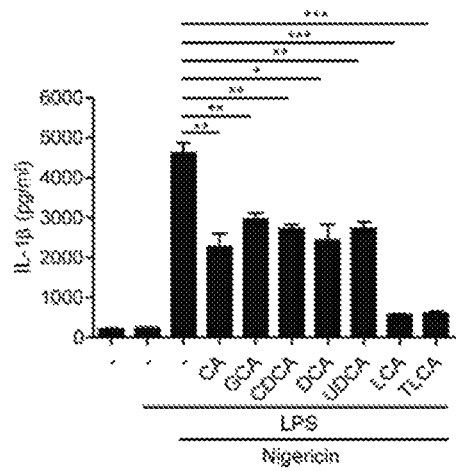
FIG. 1. Bile Acids Suppress NLRP3 Inflammasome-Mediated IL-1β Secretion. (A) lipopolysaccharide (LPS)—primed bone marrow-derived macrophages (BMDMs) were treated with the indicated bile acids (BAs) at 50 mM and then stimulated with nigericin for 45 min. Supernatants were analyzed by ELISA for IL-1β release. (B) and (C) LPS—primed BMDMs were treated with different doses of TLCA and then stimulated with nigericin for 45 min. Supernatants were analyzed by ELISA for IL-1β (B) and IL-18 (C) release. From Guo et al., 2016.
Figure 1:
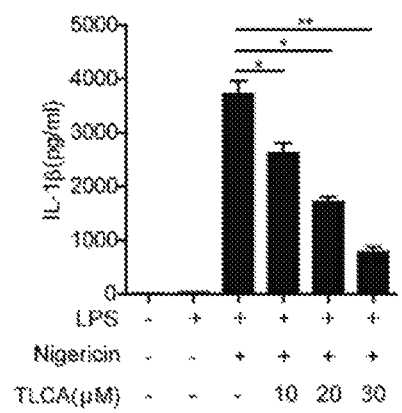
Figure 1:
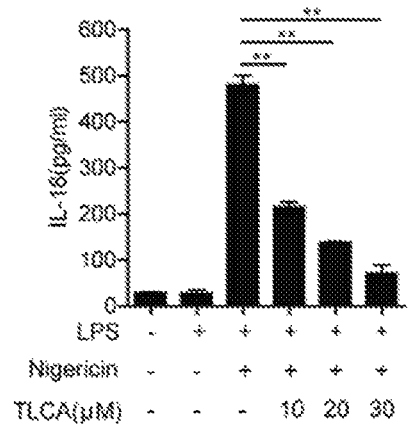

The invention is based, in part, on the finding, that the administration of an NTCP inhibitor leads to the elevation of blood bile acid levels and increase of immune-modulating signaling mediated by FXR and TGR-5. Bile acid mediated signaling through FXR and TGR5 modulates several metabolic pathways, regulating not only bile acid synthesis and enterohepatic recirculation, but also lipid, glucose and energy homeostasis. In addition, FXR and TGR5 agonists display anti-inflammatory and anti-fibrotic properties, making these agents interesting candidates for the treatment of several liver and metabolic diseases, including nonalcoholic steatohepatitis (NASH). In particular, Guo et al., 2016, demonstrate that different bile acids control inflammation and metabolic disorder through NLRP3 inflammasome inhibition. All bile acids tested by the authors exhibit such properties, but lithocholic acid (LCA) and it's taurin-conjugated form taurolithocholic acid (TLCA) were particularly effective. For example, the inhibition of pro-inflammatory cytokine IL-1β formation in macrophages was most pronounced with LCA and TLCA (FIG. 1) There is also strong evidence provided by the present inventor, that bile acid-mediated TGR5 signaling induces NRLP3 inflammasome ubiqutinilation and inhibition via adenylate-cyclase and protein kinase A (PKA) dependent pathway.

Figure 2:
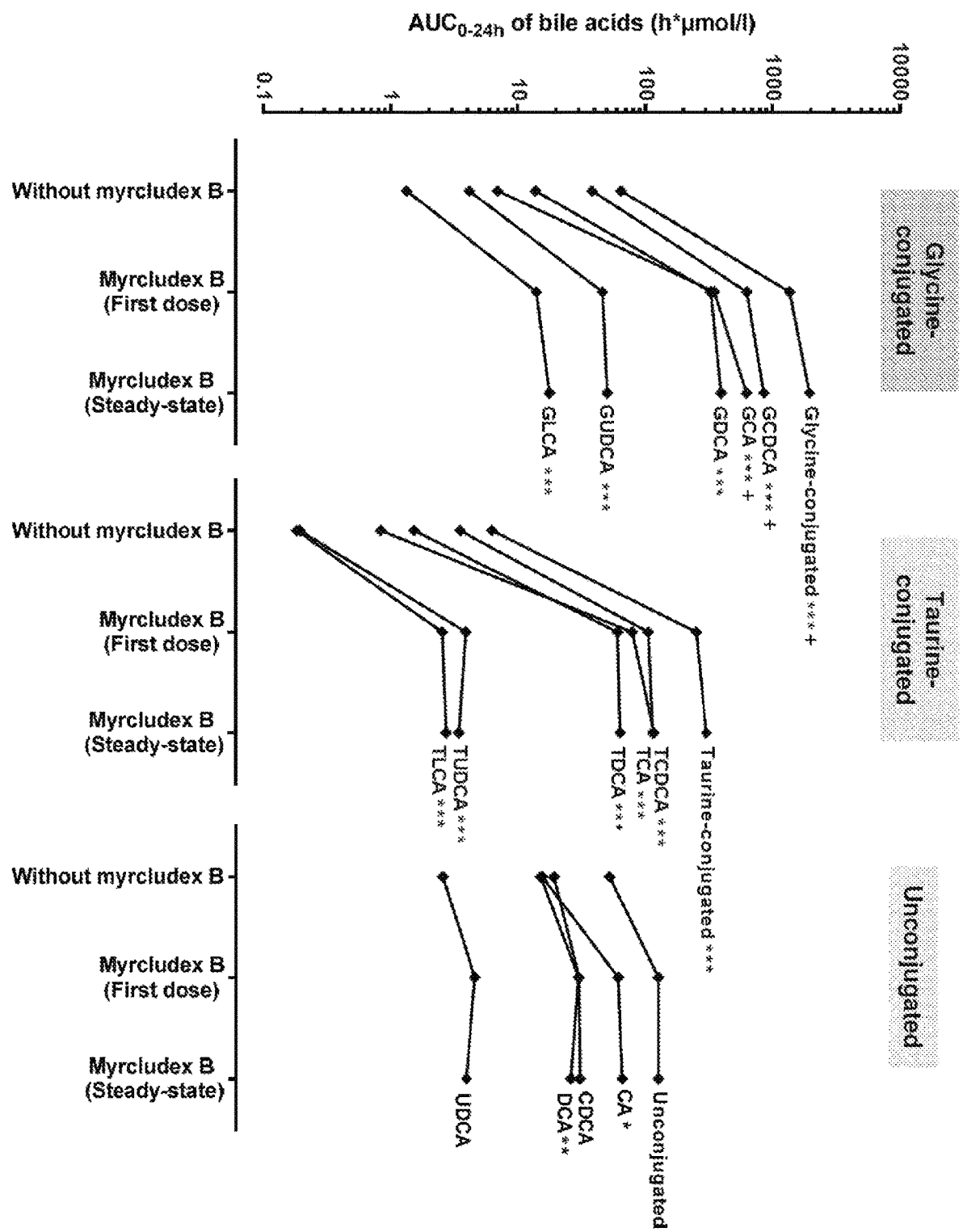
FIG. 2. Bile acid species are differentially influenced by Myrcludex B.
Figure 3:
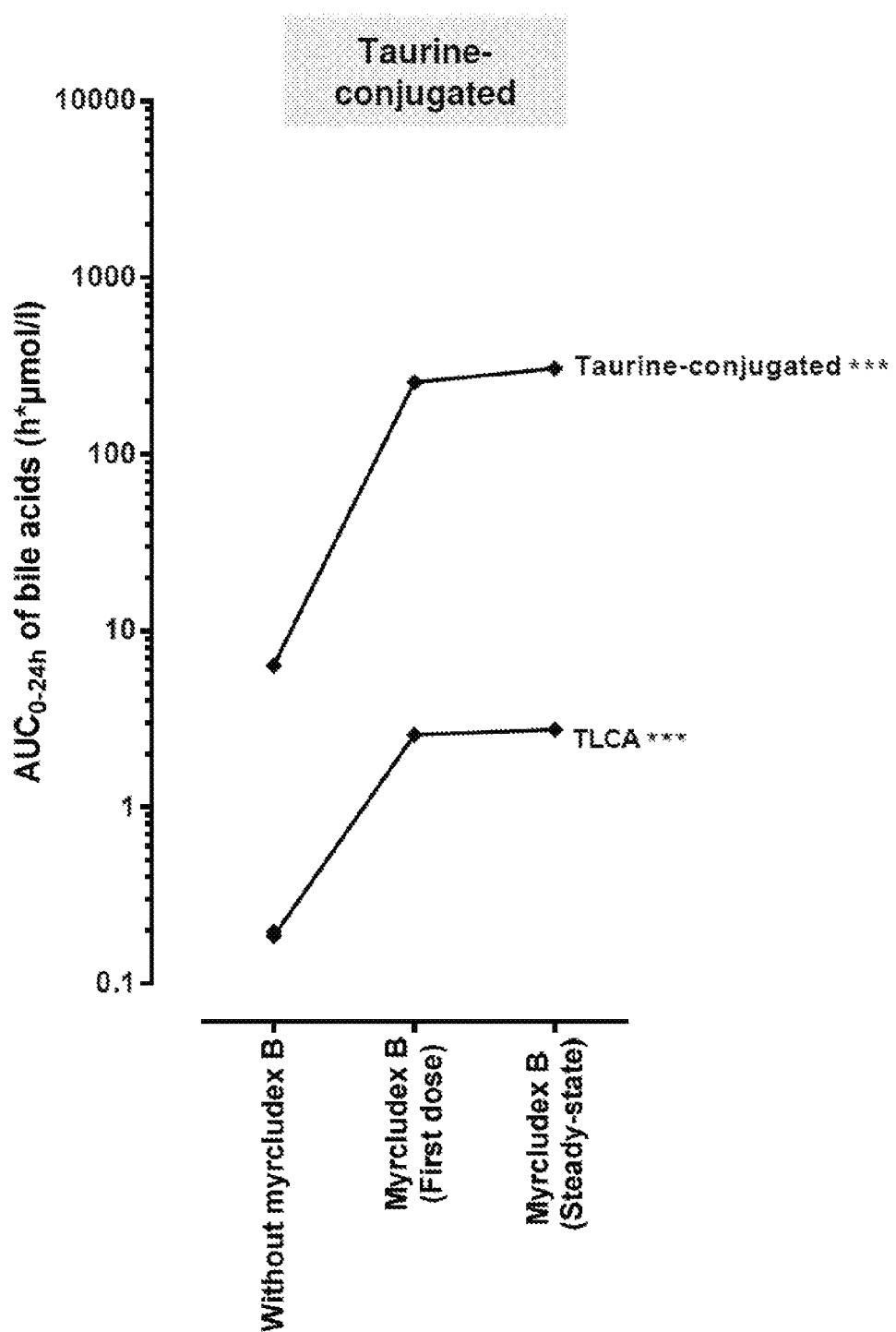
FIG. 3. TLCA elevation in response to Myrcludex B.

A clinical trial in humans completed with Myrcludex B, an NTCP-inhibiting peptide having amino acid sequence GTNL SVPNP LGFFP DHQLD PAFGA NSNNP DWDFN PNKDH WPEAN KVG (SEQ ID NO: 13), induced significant elevation of blood bile acid levels (FIG. 2), and, in particular, elevations of the TLCA level (FIG. 3). No side effects related to the bile acid elevation were associated with the treatment. Therefore, it is expected that treatment of a human subject with a NTCP inhibitor of the invention will lead to the increase of TGR5 signaling and anti-inflammatory, anti-fibrotic and other beneficial effects, resulting in the clinical benefit and disease modification for the disorders disclosed in the application.

In addition, in cholestatic disorders like PBC and primary sclerosing cholangitis, hepatocyte damage may in part be associated with accumulation of bile acids in the liver cells. The blockade of the hepatic re-uptake of the bile acids will decrease intracellular bile acid concentration and unburden hepatocytes, thus improving liver function.

The invention is further based, in part, on an unexpected finding that treatment of atherosclerosis with an inhibitor of Na+-taurocholate cotransporting polypeptide (NTCP) results in a decrease, resorption or elimination of atherosclerotic plaques. Patients with PBC are known to have high LDL levels but low evidence of atherosclerosis. The mechanism how elevated bile acids can reduce atheroscelrotic lesions is complex and includes activation of reverse cholesterol transport, induction of the respective genes, of direct detergent function of bile acids. Because NTCP is responsible for more than 50% of conjugated bile acid re-uptake from blood stream to the liver; the NTCP blockade leads to elevated bile acid levels in the blood, as observed in humans and in experimental animals. As indicated above, elevated bile acid levels were measured by the inventor in a human clinical trial using NTCP inhibitor Myrcludex B, with no side effects related to this elevation. Thus, treatment with a NTCP inhibitor may lead to clinically save elevation of bile acid levels in the blood stream and consequently to anti-atherosclerotic effect associated with elevated bile acid levels.

Accordingly, the invention provides an NTCP inhibitor for use in a method of treatment of atherosclerosis, primary biliary cirrhosis (PBC), NRLP3 inflammasome-associated diseases, including type-2 diabetes, atherosclerosis, gout, Alzheimer's disease and NASH, in a subject. Also provided is a method of treatment of aforementioned diseases in a subject by administering to the subject in need thereof an effective amount of an NTCP inhibitor. It is envisaged that administration of an NTCP inhibitor leads to an improvement, amelioration or irradiation of disease symptoms and effective treatment of the diseases.

NTCP

Sodium/bile acid cotransporter also known as the sodium/Na+-taurocholate cotransporting polypeptide (NTCP) is a protein that in humans is encoded by the SLC10A1 (solute carrier family 10 member 1) gene.

Sodium/bile acid cotransporters are integral membrane glycoproteins that participate in the enterohepatic circulation of bile acids. Two homologous transporters are involved in the reabsorption of bile acids, one absorbing from the intestinal lumen, the bile duct, and the kidney with an apical localization (SLC10A2), and the other sodium-dependent cotransporter being found in the basolateral membranes of hepatocytes (SLC10A1).

Bile formation is an important function of the liver. Bile salts are a major constituent of bile and are secreted by hepatocytes into bile and delivered into the small intestine, where they assist in fat digestion. In the liver, hepatocytes take up bile salts from the plasma and secrete them again into bile (mainly via the bile salt export pump (BSEP)) for ongoing enterohepatic circulation. Uptake of bile salts into hepatocytes occurs largely in a sodium-dependent manner by NTCP. The transport properties of NTCP have been extensively characterized. It is an electrogenic member of the solute carrier family of transporters (SLC10A1) and transports predominantly bile salts and sulfated compounds, but is also able to mediate transport of additional substrates, such as thyroid hormones, drugs and toxins. It is highly regulated under physiologic and pathophysiologic conditions. Regulation of NTCP copes with changes of bile salt load to hepatocytes and prevents entry of cytotoxic amounts of bile salts during liver disease.

For NTCP, a large range of substrates could be detected. NTCP transports unconjugated as well as taurine-conjugated and glycine-conjugated bile acids, also sulfated bile acids and, in contrast to the apical sodium dependent bile acid transporter (ASBT), also steroid sulfates, and thyroid hormones. Drugs like rosuvastatin and micafungin have also been shown to have affinity for NTCP. Recent data show FDA-approved drugs that are identified as inhibitors of NTCP. Most of them are antifungal, antihyperlipidemic (simvastatin), antihypertensive, anti-inflammatory, or glucocorticoid drugs.

Examples of bile acids which are transported into hepatocytes via NTCP are cholate; taurine- or glycine-conjugated bile acids and salts thereof (taurine- or glycine conjugated dihydroxy and trihydroxy bile salts) such as taurocholate, glycocholate, taurodeoxycholate, taurochenodeoxycholate, tauroursodeoxycholate, sulfated bile acids and salts thereof.

Without being bound by any theory or mode of action, the application teaches that blocking NTCP exerts an unexpectedly profound advantageous effect on atherosclerotic lesions such as plaques, in particular vulnerable plaques with increased rupture potential, by elevating bile acid levels in the blood. In contrast to previous treatments which primarily focused on preventive measures that were supposed to slow down the development of atherosclerotic lesions by reducing cholesterol levels, in particular the LDL levels in the blood, the treatment offered by the invention targets already existing atherosclerotic lesions and results in their significant reduction, desorption or complete elimination. Thus, the therapy provides a significant benefit for patients which could not be achieved with established therapies.

Pre-S1 Peptide Inhibitors

In one aspect, an inhibitor of Na+-taurocholate cotransporting polypeptide (NTCP) for use in a method of treatment of atherosclerosis in a subject is a pre-S1 peptide inhibitor. The pre-S1 peptide inhibitor comprises/consists of a peptide comprising amino acid sequence NPLGFX$_0$P (SEQ ID NO: 15), wherein X$_0$ is any amino acid, preferably F or L, more preferably F. It is understood that the above peptide may be at least 7, 8, 9, 10, 11, 12, 13, 14, 15, 16, 17, 18, 19, 20, 21, 22, 23, 24, 25 amino acids in length, or may be longer than that.

The pre-S1 peptide inhibitor may further comprise an N-terminal sequence of at least 4 amino acids at the N-terminus of NPLGFX$_0$P (SEQ ID NO: 15). The N-terminal sequence may consist of 4, 5, 6, 7, 8, 9, 10, 11, 12, 13, 14, 15, 16, 17, 18, or 19 amino acids. The N-terminal sequence may consist of 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19 amino acids.

At least one amino acid of the N-terminal sequence may have an amino group in a side chain. Said at least one amino acid of the N-terminal sequence is/are selected from lysine, a-amino glycine, a,y-diaminobutyric acid, ornithine, a,ß-diaminopropionic acid, preferably lysine. Said at least one amino acid of the N-terminal sequence may be located at the N-terminus of the N-terminal sequence. The at least one amino acid of the N-terminal sequence is 1, 2, 3, 4, 5, 6, 7, 8, 9, 10 or 11 amino acids, or wherein the at least one amino acid of the N-terminal sequence is 1 to 3, 1 to 4, 1 to 5, 1 to 6, 1 to 7, 1 to 8, 1 to 9, or 1 to 10 amino acids.

The N-terminal sequence may comprise amino acid sequence NX$_1$SX$_2$X$_3$ (SEQ ID NO: 16), wherein X$_1$, X$_2$ and X$_3$ is any amino acid. It is preferred that in NX$_1$SX$_2$X$_3$ (SEQ ID NO: 16):

X$_1$ is L, I or Q, preferably L;

X$_2$ is T, V, A or is absent, preferably T or V, more preferably T; and/or

X$_3$ of is P, S, T or F, preferably P or S, more preferably S.

The amino acid sequence NX$_1$SX$_2$X$_3$ (SEQ ID NO: 16) may be directly attached to the N-terminus of NPLGFX$_0$P (SEQ ID NO: 15).

Thus, the pre-S1 peptide inhibitor may comprise amino acid sequence NX$_1$SX$_2$X$_3$NPLGFX$_0$P (SEQ ID NO: 17), wherein X$_0$ is any amino acid;

X$_1$ is L, I or Q, preferably L;

X$_2$ is T, V, A or is absent, preferably T or V, more preferably T; and

X$_3$ of is P, S, T or F, preferably P or S, more preferably S.

The pre-S1 peptide inhibitor may further comprise a C-terminal sequence of at least 1 amino acid at the C-terminus of NPLGFX$_0$P (SEQ ID NO: 15).

The C-terminal sequence may consist of 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92 or 93 amino acids. The C-terminal sequence may consist of 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, 1 to 30, 1 to 31, 1 to 32, 1 to 33, 1 to 34, or 1 to 35 amino acids.

The C-terminal sequence may comprise amino acid sequence X$_4$HQLDP (SEQ ID NO: 18), wherein X$_4$ is any amino acid. It is preferred that X$_4$ is D, E or S, preferably D or E, more preferably D.

The amino acid sequence X$_4$HQLDP (SEQ ID NO: 18) may be directly attached to the C-terminus of NPLGFX$_0$P (SEQ ID NO: 15).

Thus, the pre-S1 peptide inhibitor may comprise amino acid sequence NPLGFX$_0$PX$_4$HQLDP (SEQ ID NO: 19), wherein X$_0$ is any amino acid; and X$_4$ is D, E or S, preferably D or E, more preferably D.

The pre-S1 peptide inhibitor may comprise both the N-terminal and the C-terminal sequences. Thus, the pre-S1 peptide inhibitor may comprise amino acid sequence NX$_1$SX$_2$X$_3$NPLGFX$_0$PX$_4$HQLDP (SEQ ID NO: 20), wherein X$_0$ is any amino acid;

X$_1$ is L, I or Q, preferably L;

X$_2$ is T, V, A or is absent, preferably T or V, more preferably T;

X$_3$ of is P, S, T or F, preferably P or S, more preferably S; and

X$_4$ is D, E or S, preferably D or E, more preferably D.

The pre-S1 peptide inhibitor may comprise/consist of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids.

The pre-S1 peptide inhibitor may also comprise a pre-S1 peptide of an HBV virus, or a functional fragment thereof. It is preferred that the function is binding to NTCP, inhibition of NTCP, or reduction of NTCP activity.

Hepatitis B viruses (HBVs) are small, enveloped DNA viruses that replicate their genome via reverse transcription of a pre-genomic RNA transcript in the cytoplasm of infected hepatocytes. They are classified into the family Hepadnaviridae and are adapted to mammals (primates and rodents) and birds, where they cause acute and persistent infections. From studies in a HBV-susceptible cell line HepaRG and systems based on primary human hepatocytes (PHH) and primary *Tupaia belangeri* hepatocytes it became clear that viral infectivity can be assigned to different subdomains in two of the three viral envelope proteins. The three HBV envelope proteins are termed L (large), M (middle) and S (small). They form a proteinaceous outer virus shell, which is embedded in an endoplasmic reticulum (ER)-derived lipid bilayer. Their coding mRNAs originate from one single open reading frame. Since their three start codons are in phase, they share the C-terminal 226 amino acids long S-domain which anchor the proteins via four putative transmembrane helices (TM domains) in the lipid bilayer. The S protein drives particle formation and accordingly serves an important function in virus assembly. The S domain has further been shown to participate in virus entry. Linked to the N terminus of the S domain, the M and L proteins bear two hydrophilic extensions, one of 55 amino acids and, depending on genotype, one of 108 (genotype D), 118 (genotypes E and G), or 119 (genotypes A, B, C, F, H) amino acids called pre-S2 (M) and pre-S1 (L), respectively. The L proteins of all hepadnaviruses contain recognition motifs for N-myristoyltransferase and are accordingly subjected to this modification. Crucial elements for virus attachment, specific receptor binding, or fusion have been identified within the L, M, and S proteins.

Peptides derived from HBV pre-S1 polypeptide have been previously identified as inhibitors of virus entry into the cell (hepatocyte), i.e., HBV/HDV entry inhibitors. An example of an HBV/HDV entry inhibitor presently undergoing clinical trials is a linear 47-amino acid chemically synthesized peptide (known under the trade name Myrcludex B) which is derived from the pre-S1 domain of the large (L) HBV surface protein, composed of naturally occurring L-amino acids and bearing an N-terminal myristoyl moiety and a C-terminal carboxamide.

According to the invention, these pre-S1-derived peptides can be used as NTCP inhibitors, i.e., as pre-S1 peptide inhibitors.

Thus, a pre-S1 peptide inhibitor for use according to the invention may be derived from N-terminal domain of the large (L) HBV surface protein, pre-S1, of any HBV virus, in particular of any HBV strain, genotype or subtype. Examples of HBVs are human HBV, gorilla HBV, chimpanzee HBV, woodchuck HBV, Woolly Monkey HBV (WMHBV). Examples of HBV strains are HBV strain alphal and HBV strain LSH (chimpanzee isolate). Examples of HBV subtypes are AD, ADR, ADW, ADYW, AR and AYW. Examples of HBV genotypes are genotypes A to H of human HBV. According to the standard HBV nomenclature, pre-S1 peptide has amino acid coordinates between −11 and 108. Compared to genotype D, all other genotypes contain an additional 10 (E and G) or 11 (A, B, C, F, and H) N-terminal pre-S1 amino acids. Accordingly, a viral pre-S1 peptide may have different amino acid coordinates and hence a different length, depending on the viral stain, genotype or subtype.

The sequence alignment also indicates that pre-S1 peptides of various genotypes share conserved regions along the peptide length. A highly conserved region is situated between amino acid positions 9 to 21. In addition, individual highly conserved amino acids are situated between amino acids 2 and 6. These conserved sequences are also present in the hepatitis B viruses isolated from chimpanzee, gorilla, and woolly monkey.

Experimental evidence indicate that the capacity of synthetic HBV pre-S1-derived peptides to interfere with the HBV infection depends on the presence of some amino acids within conserved the preS-1 regions. Thus, of importance for the peptide activity is a region between amino acid positions 9 and 15 of pre-S1 and in particular amino acids 11, 12, 13, 14 and/or 15 within this region. Further, replacement of some amino acids within a region between positions 2 and 9 are reduced the HBV inhibitory activity of a pre-S1 peptide, whereby amino acid 9 appears essential. Further regions that may contribute to the inhibitory activity of HBV pre-S1-derived peptides are amino acids 2 to 8, 16 to 20, and, to a less pronounced extent, 34 to 48. These conserved amino acids are also important for the ability of the pre-S1 peptide to inhibit NTCP.

Thus, the pre-S1 peptide inhibitors may span amino acids −11 to 108 of HBV pre-S1 (entire HBV pre-S1) or any portion within this region. Hereinafter reference will be made to the standard HBV amino acid numbering. In particular, the pre-S1 peptide inhibitor may span amino acids −11 to 78. In some genotypes, the first 10 (genotypes E and G) or 11 (genotypes A, B, C, F, and H) amino acids are absent. Accordingly, the pre-S1 peptide inhibitor may span amino acids 1 to 78 of HBV. One or more amino acids beyond amino acid 48, i.e., from amino acid 49 to 108 may be absent. Accordingly, the pre-S1 peptide inhibitor may span amino acids −11 to 48. Within the range of −11 to 48, the first 1, 2, 3, 4, 5, 6, 7, 8, 9, 10 or 11 amino acids may be dispensed with. Accordingly, the pre-S1 peptide inhibitor may span amino acids 1 to 48. Amino acid 1 (Met) may be absent. Respective pre-S1 peptide inhibitor may span amino acids 2 to 48 and optionally comprise further amino acids at the C-terminus. Within the region of 2 to 48, amino acids 2 to 21 and 34 to 48 are more important for pre-S1 peptide inhibitor function than amino acids 21 to 33. Amino acids 9 to 15, in particular 11 to 15 are most important. Accordingly, the pre-S1 peptide inhibitor may consist of amino acids 2 to 48 or a truncated portion thereof. Alternatively, the pre-S1 peptide inhibitor may comprise amino acids 2 to 48 or a truncated portion thereof.

A truncated portion may be obtained by amino acid deletions from either end of pre-S1 peptide and have a length of between 46 and 7 amino acids. In particular, a truncated portion may have a length of 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, or 7 amino acids.

A truncated portion preferably comprises amino acids 9 to 15, 10 to 15, or 11 to 15. A truncated portion preferably consists of amino acids 11 to 15. A truncated portion may gradually be extended by addition of amino acids flanking amino acids 11 to 15. For example, a truncated portion may consists of amino acids 2 to 15, 3 to 15, 4 to 15, 5 to 15, 6 to 15, 7 to 15, 8 to 15, 9 to 15 or 10 to 15. Any of amino acids 16 to 48 may be used in this example to provide further truncated portions.

In another example, a truncated portion may consist of amino acids 2 to 15, 2 to 16, 2 to 17, 2 to 18, 2 to 19, 2 to 20, 2 to 21, 2 to 22, 2 to 23, 2 to 24, 2 to 25, 2 to 26, 2 to 27, 2 to 28, 2 to 29, 2 to 30, 2 to 31, 2 to 32, 2 to 33, 2 to 34, 2 to 35, 2 to 36, 2 to 37, 2 to 38, 2 to 39, 2 to 40, 2 to 41, 2 to 42, 2 to 43, 2 to 44, 2 to 45, 2 to 45, 2 to 46, 2 to 47 or 2 to 48. Any of amino acids 3 to 11 may be used in this example to provide further truncated portions.

Further examples of truncated portions are amino acids 9 to 15, 2 to 21, 5 to 21, 2 to 15, 2 to 20, 2 to 25, 2 to 30, 2 to 35, 2 to 40.

NPLGFX$_0$P (SEQ ID NO: 15) comprised in the pre-S1 peptide inhibitor described above corresponds to amino acid position 9 to 15 of an pre-S1 peptide of an HBV virus.

A truncated portion of pre-S1 peptide may be a functional fragment of pre-S1 peptide retaining the function of pre-S1 peptide in binding and/or inhibiting NTCP.

Thus, the pre-S1 peptide inhibitor for use according to the invention may comprise or consists of:

at least amino acids 9 to 15, 8 to 15, 7 to 15, 6 to 15, 5 to 15, 4 to 15, 3 to 15, 2 to 15 of a pre-S1 peptide of an HBV virus;

at least amino acids 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 9 to 31, 9 to 32, 9 to 33, 9 to 34, 9 to 35, 9 to 36, 9 to 37, 9 to 38, 9 to 39, 9 to 40, 9 to 41, 9 to 42, 9 to 43, 9 to 44, 9 to 45, 9 to 46, 9 to 47, 9 to 48 of a pre-S1 peptide of an HBV virus;

at least amino acids 8 to 16, 7 to 17, 6 to 18, 5 to 19, 4 to 20, 3 to 21, or 2 to 22 of a pre-S1 peptide of an HBV virus;

at least amino acids 2 to 15, 2 to 16, 2 to 17, 2 to 18, 2 to 19, 2 to 19, 2 to 20, 2 to 21, 2 to 22, 2 to 23, 2 to 24, 2 to 25 2 to 26, 2 to 27, 2 to 28, 2 to 29, 2 to 30, 2 to 31, 2 to 32, 2 to 33, 2 to 34, 2 to 35, 2 to 36, 2 to 37, 2 to 38, 2 to 39, 2 to 40, 2 to 41, 2 to 42, 2 to 43, 2 to 44, 2 to 45, 2 to 46, 2 to 47, or 2 to 48 of a pre-S1 peptide of an HBV virus;

at least amino acids 9 to 15 and 16 to 20 of a pre-S1 peptide of an HBV virus;

at least amino acids 2 to 8 and 9 to 15 of a pre-S1 peptide of an HBV virus;

at least amino acids 2 to 8, 9 to 15 and 16 to 20 of a pre-S1 peptide of an HBV virus;

at least amino acids 9 to 15 and 34 to 48 of a pre-S1 peptide of an HBV virus;

at least amino acids 9 to 15, 16 to 20 and 34 to 48 of a pre-S1 peptide of an HBV virus;

at least amino acids 2 to 8, 9 to 15 and 34 to 48 of a pre-S1 peptide of an HBV virus;

at least amino acids 2 to 8, 9 to 15, 16 to 20 and 34 to 48 of a pre-S1 peptide of an HBV virus;

at least amino acids 2 to 48 of a pre-S1 peptide of an HBV virus or a portion thereof of at least 15 amino acids; or amino acids 2 to 48 of a pre-S1 peptide of an HBV virus.

The pre-S1 peptide inhibitor may also be a sequence having at least 50%, 55%, 60%, 65%, 70%, 75%, 80%, 85%, 90%, or 95% identity with any of the above sequences.

The pre-S1 peptide inhibitors may be derived from pre-S1 peptides of various HBV viruses, e.g., various genotypes, strains or subtypes. In particular, pre-S1 peptide inhibitors may be derived from pre-S1 of genotypes A, B, C, D, E, F, G or H, or of subtypes AD, ADR, ADW, ADYW, AR and AYW. Pre-S1 peptides from various HBV viruses will usually be homologues. Homologues from various species have structural and functional similarity and usually share a common evolutionary ancestor. It is envisioned that pre-S1 homologues from further genotypes, strains or subtypes to be identified in the future will be equally suitable as pre-S1 peptide inhibitors. The pre-S1 peptide inhibitors may also be derived from a pre-S1 consensus sequence.

Examples of HBV pre-S1 sequences between amino acids −11 or −10 or 1 (depending on the genotype) and 48 of various genotypes and the consequence sequence are provided below:

```
HBV pre-S1 consensus sequence (positions (-11)
to 48)
                                    (SEQ ID NO: 1)
(-11)-M GGWSS TPRKG MGTNL SVPNP LGFFP DHQLD PAFRA

NSNNP DWDFN PNKDH WPEAN  KVG-48

HBV pre-S1 Genotype A sequence (positions (-11)
to 48)
                                    (SEQ ID NO: 2)
(-11)-M GGWSS KPRKG MGTNL SVPNP LGFFP DHQLD PAFGA

NSNNP DWDFN PVKDD WPAAN QVG-48

HBV pre-S1 Genotype B sequence (positions (-11)
to 48)
                                    (SEQ ID NO: 3)
(-11)-M GGWSS KPRKG MGTNL SVPNP LGFFP DHQLD PAFKA

NSENP DWDLN PHKDN WPDAN KVG-48

HBV pre-S1 Genotype C sequence (positions (-11)
to 48)
                                    (SEQ ID NO: 4)
(-11)-M GGWSS KPRQG MGTNL SVPNP LGFFP DHQLD PAFGA

NSNNP DWDFN PNKDH WPEAN QVG-48

HBV pre-S1 Genotype D sequence (positions 1 to 48)
                                    (SEQ ID NO: 5)
1-MGQNL STSNP LGFFP DHQLD PAFRA NTANP DWDFN PNKDT

WPDAN KVG-48

HBV pre-S1 Genotype E sequence (positions (-10)
to 48)
                                    SEQ ID NO: 6)
(-10)-MGLSW TVPLE WGKNI STTNP LGFFP DHQLD PAFRA

NTRNP DWDHN PNKDH WTEAN KVG-48

HBV preS1 Genotype F sequence (positions (-11)
to 48)
                                    (SEQ ID NO: 7)
(-11)-M GAPLS TTRRG MGQNL SVPNP LGFFP DHQLD PLFRA

NSSSP DWDFN TNKDS WPMAN KVG-48

HBV pre-S1 Genotype G sequence (positions (-10)
to 48)
                                    (SEQ ID NO: 8)
(-10)-MGLSW TVPLE WGKNL SASNP LGFLP DHQLD PAFRA

NTNNP DWDFN PKKDP WPEAN KVG-48

HBV preS1 Genotype H sequence (positions (-11)
to 48)
                                    (SEQ ID NO: 9)
(-11)-M GAPLS TARRG MGQNL SVPNP LGFFP DHQLD PLFRA

NSSSP DWDFN TNKDN WPMAN KVG-48
```

The pre-S1 sequence between amino acids 1 and 48 from Woolly Monkey WMHBV is provided below:
1-MGLNQ STFNP LGFFP SHQLD PLFKA NAGSA DWDKN PNKDP WPQAH DTA (SEQ ID NO: 10)

The pre-S1 peptide inhibitors may contain one or more (e.g., 1, 2, 3, 4, 5, 6, 7, 8 9, or 10) amino acid substitutions which do not substantially reduce their NTCP inhibitory activity. Preferably, NTCP inhibitory activity should not be reduced by more than two orders of magnitude. In particular, reduction by 2-, 3-, 4-, 5-, 6-, 7-, 8-, 9-, 10-, 11-, 12-, 13-, 14-, 15-, 16-, 17-, 18-, 19-, or 20-fold is tolerated. The NTCP inhibitory activity may be measured in terms of $IC_{50}$ or $IC_{90}$. Amino acid substitutions may be conservative or non-conservative Amino acid substitutions preferably do not affect amino acids important for the NTCP inhibitory activity of pre-S1 peptide inhibitors. Individual amino acids located within a highly conserved part of pre-S1 spanning amino acids 2 to 21 are more important for the activity than amino acids outside this region. Within this region, amino acids 9 to 15 are even more important. Among these, amino acids 9, 11, 12 and 13 are most important. Accordingly, amino acid substitutions are preferably located outside amino acids 11 to 15, 9 to 15, 5 to 15, or 2 to 15 Amino acid substitutions may also be located outside amino acids 2 to 8, 16 to 20 or 34 to 48 Amino acid substitutions may be located within amino acids 20 to 23, 26 to 32.

An example of a pre-S1 sequence derived from the pre-S1 sequence of genotype C and containing an amino acid substitution at position 46 (Gln (Q)→Lys (K)), according to the standard HBV nomenclature, is provided below:

```
                                        (SEQ ID NO: 11)
(-11)-M GGWSS KPRQG MGTNL SVPNP LGFFP DHQLD PAFGA

NSNNP DWDFN PNKDH WPEAN KVG-48.
```

A preferred pre-S1 peptide inhibitor is based on pre-S1 peptide between positions 2 and 48 (according to the standard HBV nomenclature) of the amino acid sequence of the HBV pre-S1 consensus sequence:

```
                                        (SEQ ID NO: 12)
   GTNL SVPNP LGFFP DHQLD PAFRA NSNNP DWDFN PNKDH

WPEAN KVG.
```

Another preferred pre-S1 peptide inhibitor is based on pre-S1 peptide between positions 2 and 48 (according to the standard HBV nomenclature) of the amino acid sequence of the HBV preS1 Genotype C:

```
                                        (SEQ ID NO: 14)
   GTNL SVPNP LGFFP DHQLD PAFGA NSNNP DWDFN PNKDH

WPEAN QVG
```

A most preferred peptide inhibitor is based on pre-S1 peptide between positions 2 and 48 (according to the standard HBV nomenclature) of the amino acid sequence of genotype C with an amino acid substitution at position 46 (Gln (Q)→Lys (K))

```
                                        (SEQ ID NO: 13)
   GTNL SVPNP LGFFP DHQLD PAFGA NSNNP DWDFN PNKDH

WPEAN KVG.
```

A pre-S1 peptide inhibitor may be an N-terminally or C-terminally truncated portion of the above pre-S1 inhibitors of at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 amino acids. The portion retains its functionality as NTCP inhibitor or NTCP binding protein.

The pre-S1 peptide inhibitor may be a sequence having at least 50%, 55%, 60%, 65%, 70%, 75%, 80%, 85%, 90%, or 95% identity with any of the above sequences.

Pre-S1 peptide inhibitors are preferably hydrophobic. They may be modified by at least one hydrophobic moiety. Hydrophobic modification by acylation is preferred. Acylation may be acylation with carboxylic acids, fatty acids, or amino acids with lipophilic side chains. Alternatively, pre-S1 peptide inhibitors may be modified by cholesterol, derivatives of cholesterol, phospholipids, glycolipids, glycerol esters, steroids, ceramids, isoprene derivatives, adamantine, farnesol, aliphatic groups, or polyaromatic compounds. Fatty acids may be saturated or unsaturated fatty acids, branched or unbranched fatty acids, preferably with 8 to 22 carbon atoms. Examples of suitable fatty acids for acylation are myristic acid (D14), stearic acid (C18), palmitic acid (C16). Acylation with myristoyl is preferred. Variation of hydrophobic moiety allows for the modulation of specific pre-S1 peptide inhibitor activities.

A hydrophobic moiety is preferably attached to the N-terminus of the pre-S1 peptide inhibitor or in 1, 2, 3, or 4 amino acids proximity to the N-terminus. Thus, a hydrophobic moiety may be attached to the N-terminal amino acid of the pre-S1 peptide inhibitor, or to an amino acid in close proximity to the N-terminus, e g amino acids −5, −4, −3, −2, −1, 1, 2, 3, 4, or 5. More than one hydrophobic moiety may be used for the modification of pre-S1 peptide inhibitor. The hydrophobic moieties can be identical or different. The attachment of the hydrophobic moieties is preferably by covalent binding, which can be achieved via carbamate, amide, ether, disulfide or any other linkage that is within the skill of the person skilled in the art.

A preferred peptide inhibitor is a pre-S1 peptide of amino acid sequence

```
                                        (SEQ ID NO: 13)
   GTNL SVPNP LGFFP DHQLD PAFGA NSNNP DWDFN PNKDH

WPEAN KVG,
``` which is modified at the N-terminus by myristoyl or stearoyl.

The chemical name of the pre-S1 peptide inhibitor Myrcludex B is

N-Myristoyl-glycyl-L-threonyl-L-asparaginyl-L-leucyl-L-seryl-L-valyl-L-prolyl-L-asparaginyl-L-prolyl-L-leucyl-glycyl-L -phenylalanyl-L-phenylalanyl-L-prolyl-L-aspartyl-L-histidyl-L-glutaminyl-L-leucyl-L-aspartyl-L-prolyl-L-alanyl-L-phenylalanyl -glycyl-L-alanyl-L-asparaginyl-L-seryl-L-asparaginyl-L-asparaginyl-L-prolyl-L-aspartyl-L-tryptophanyl-L-aspartyl-L-phenylalanyl -L-asparaginyl-L-prolyl-L-asparaginyl-L-lysyl-L-aspartyl-L-histidyl-L -tryptophanyl-L-prolyl-L-glutamyl-L-alanyl-L-asparaginyl-L-lysyl-L-valyl-glycinamide, acetate salt.

An abbreviated chemical name of Myrcludex B is

Myristoyl-Gly-Thr-Asn-Leu-Ser-Val-Pro-Asn-Pro-Leu-Gly-Phe-Phe-Pro-Asp-His-Gln-Leu-Asp-Pro-Ala-Phe-Gly-Ala-Asn-Ser-Asn-Asn-Pro-Asp-Trp-Asp-Phe-Asn-Pro-Asn-Lys-Asp-His-Trp-Pro-Glu-Ala-Asn-Lys-Val-Gly-NH2, acetate salt.

Pre-S1 peptide inhibitors may further be modified in a conventional way to improve peptide stability, e.g. stability against degradation. Such modification may take place at the C-terminus or in 1, 2, 3, or 4 amino acids proximity to the C-terminus. The modification may include a modification with a protective moiety such as amide, D-amino acid, modified amino acid, cyclic amino acid, natural polymer, synthetic polymer, or glycan. Modification with PEG is an example. It is preferred that the protective moiety is an amid. The protective moiety may be linked to the amino acid of the pre-S1 peptide inhibitor via a linker. The linker may be polyalanine, polyglycin, carbohydrates, or $(CH_2)_n$ groups, wherein n is at least 1.

It is preferred that the pre-S1 peptide inhibitor consists of amino acid sequence 2 to 48 of genotype C preS1 peptide which is modified at the N-terminus by myristoylation and further modified at the C-terminus with amide.

The preferred pre-S1 peptide inhibitor for the use according to the invention is Myrcludex B

```
Myr-GTNLSVPNPLGFFPDHQLDPAFGANSNNPDWDFNPNKDHWPEANK

VG-amide.
```

According to the invention, pre-S1 peptide inhibitor may be administered to the subject, preferably human:

at a dose such that the concentration of the pre-S1 peptide inhibitor at the NTCP site, i.e., in hepatocytes, is equal or above a Ki of about 1 to 10 nM;

at a daily dose of between 0.1 mg and 50 mg, 0.5 mg and 20 mg per day, 1 mg to 15 mg, 1 mg to 10 mg, 1 mg to 5 mg, preferably 2 mg, 3 mg, 4 mg, 5 mg, 6 mg, 7 mg, 8 mg, 9 mg or 10 mg per day; or at a daily dosage of between about 0.0014 mg/kg body weight and about 0.7 mg/kg body weight, preferably between about 0.014 mg/kg body weight to about 0.28 mg/kg body weight (1 mg to 20 mg).

A unit dose of a pre-S1 peptide inhibitor such as Myrcludex B in the combination or composition may be between 0.5 mg and 20 mg, for example 1 mg, 2 mg, 3 mg, 4, mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg, preferably 2 mg, 5 mg, or 10 mg.

The pre-S1 peptide inhibitor may be administered to the subject, preferably human, for 2 weeks, 3, weeks, 4 weeks, 5 weeks, 6 weeks, 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3 years, or 4 years or longer. The duration of administration will depend on the progression of the treatment and side effects.

The pre-S1 peptide inhibitor may be administered to the subject, preferably human subject, subcutaneously, intravenously, orally, nasally, intramuscularly, transdermally, by inhalation or suppository, preferably intravenously or subcutaneously, most preferably subcutaneously.

The pre-S1 peptide inhibitor may be administered to the subject, preferably human, at various doses, treatment schedules and routes of administration as described above. For example, the invention provides following treatment regimens for Myrcludex B:

2 mg Myrcludex B given daily for 24 weeks. The course may be followed by the administration of 2 mg daily Myrcludex B for another 24 weeks. Myrcludex B may be delivered subcutaneously. In this example, the daily Myrcludex B dose may also be 5 mg or 10 mg.

2 mg Myrcludex B given daily. The treatment may last 48 weeks. In this example, the daily Myrcludex B dose may also be 5 mg or 10 mg.

2 mg Myrcludex B given daily. The treatment may last for 2 years or longer (indefinitely). In this example, the daily Myrcludex B dose may also be 5 mg or 10 mg.

2 mg Myrcludex B may given daily in combination. The treatment may last at least 48 weeks. In this example, the daily Myrcludex B dose may be 5 mg or 10 mg.

5 mg Myrcludex B may be given daily for 24 weeks or for 48 weeks.

Further NTCP Inhibitors

For the purposes of the invention, an NTCP inhibitor may be an agent or compound other than pre-S1 peptide that is capable of inhibiting the activity or production of NTCP.

An NTCP inhibitor may be selected from bendroflumethiazide, ezetimibe, simvastatin, nitrendipine, rosuvastatin, nefazodone, indomethacin, nifedipine, tioconazole, methylprednisolone, prochlorperazine, nateglinide, irbesartan, losartan, olmesartan, fenofibrate, candesartan, cyclosporin A, cyclosporin B, non-immunosupressive cyclosporin A analogues, progesterone, propranolol, bosentan, or a combination thereof.

An NTCP inhibitor may further comprise an siRNA targeting the gene encoding NTCP, wherein the siRNA comprises a nucleotide sequence set forth in siRNA-1 to siRNA-4 targeting tupaia SLC10A1 gene, or siRNA-11, siRNA-405, siRNA-406, siRNA-pool(4), siRNA-pool(5), siRNA-pool(6) or siRNA-pool(7) targeting human SLC10A1 gene. The anti-NTCP agent comprises an antisense RNA targeting the gene encoding NTCP.

Sometimes, an NTCP inhibitor inhibits or modifies a nuclear factor that controls NTCP transcription. For example, the agent may be TTNPB, a panRAR agonist, all-trans retinoic acid (ATRA), 9-cis retinoic acid (9CRA), etc.

Alternatively, an NTCP inhibitor inhibits or modifies a histone or genomic DNA modification that controls NTCP transcription. DNA methylation inhibitors, including nucleoside analogs of cytosine, such as 5-azacytidine, 5-aza-2'-deoxycytidine (5-azadC); MG98 (an antisense oligodeoxynucleotide directed against the 3' untranslated region of the DNA methyltransferase-1 enzyme mRNA); histone deacetylase inhibitors (HDAC inhibitors, HDI), such as vorinostat (suberoylanilide hydroxamic acid; SAHA), and mocetinostat (MGCD0103), are all contemplated as NTCP inhibitors for use according to the invention.

An NTCP inhibitor may inhibit or modify the phosphorylation and/or glycosylation of NTCP, such as Tunicamysin, which is a mixture of homologous nucleoside antibiotics, which blocks all N-glycosylation of proteins. In some instances, the agent is a PI3K inhibitor, e.g., L Y294002, wortmannin, etc.

An NTCP inhibitor may comprise an antibody that specifically binds to NTCP. The antibody may specifically bind to a portion of NTCP that interacts with HBV and/or HDV, e.g., an epitope in the extracellular domains. In some embodiments, the extracellular domain comprises amino acids 17-27, 73-89, 142-152, 207-217 or 275-278 of NTCP.

An NTCP inhibitor may comprise a variant form of NTCP, wherein the variant form of NTCP is selected from the group consisting of a mutant NTCP, a fragment of NTCP and a soluble NTCP polypeptide. The fragment may comprise an extracellular domain of NTCP.

An NTCP inhibitor may comprise an NTCP substrate or an NTCP substrate derivative or analogue. It is preferred that the NTCP substrate comprises a bile acid, wherein the bile acid is selected from the group consisting of taurolithocholate, cholic acid, chenodeoxycholic acid, glycocholic acid, taurocholic acid, deoxycholic acid, lithocholic acid, ursodeoxycholic acid and hyodeoxycholic acid.

An anti-NTCP inhibitor may further be a members of the pyrrolotriazinyl class of insulin-like growth factor type 1 receptor (IGF-1R) kinase inhibitors such as defined as formula I in U.S. Pat. No. 7,534,792, especially BMS-754807. This preferred compound is (S)-1-(4-(5-cyclopropyl-1H-pyrazol-3-ylamino)pyrrolo[1,2-f][1,2,4]triazin-2-yl)-N-(6-fluoropyridin-3-yl)-2-methylpyrrolidine-2-carboxamide.

The compounds of formula I are as follows:

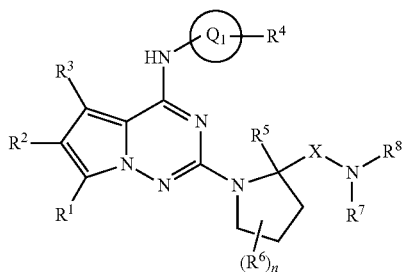

wherein $Q^1$, is aryl, substituted aryl, heteroaryl, or substituted heteroaryl;

X is C=O, C=S, C=NR$^9$, or CH$_2$;

$R^1$, $R^2$, and $R^3$ are independently hydrogen, alkyl, substituted alkyl, cycloalkyl, substituted cycloalkyl, hydroxy, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl, or alkylcarbonyl;

$R^4$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^5$ is hydrogen, halogen, cyano, alkyl, or substituted alkyl;

$R^6$ is independently hydrogen, alkyl, substituted alkyl, alkylidene, substituted alkylidene, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

n is 0, 1, 2, 3, 4, 5, or 6; or when n is 2 and $R^6$ are geminal substituents, they may together form an optionally substituted 3-6 membered saturated or unsaturated carbocyclic or heterocyclic ring; or when n is 2 and $R^6$ are 1,2-cis substituents, they may together form an optionally substituted 3-6 membered fused saturated carbocyclic or heterocyclic ring; or when n is 2 and $R^6$ are 1,3-cis substituents they may together form an optionally substituted 1-4 membered alkyl or heteroalkyl bridge; or when there are two $R^6$'s on the same carbon, they may together form a carbonyl (C=O) or alkylidene group (C=CHR$^9$);

$R^7$ and $R^8$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl, or $R^7$ and $R^8$ may be taken together to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

$R^9$ is hydrogen or lower alkyl;

or a pharmaceutically acceptable salt, tautomer, or stereoisomer thereof.

In another embodiment, the compounds of formula I are those wherein, independently, $R^1$, $R^2$, $R^3$ and $R^4$ is each H;

$Q^1$ is aryl or heteroaryl;

$R^5$, $R^6$, $R^7$ $R^8$ and $R^9$ is each independently H or lower alkyl; and

X is CH$_2$, C=O, or C=N R$^9$;

or a pharmaceutically acceptable salt, tautomer, or stereoisomer thereof.

"Alkyl" refers to straight or branched chain unsubstituted hydrocarbon groups of 1 to 20 carbon atoms, preferably 1 to 7 carbon atoms.

"Lower alkyl" refers to unsubstituted alkyl groups of 1 to 4 carbon atoms.

"Substituted alkyl" refers to an alkyl group substituted by one to four substituents, such as, halo, hydroxy, alkoxy, oxo, alkanoyl, aryloxy, alkanoyloxy, amino, alkylamino, arylamino, arylalkylamino, disubstituted amino in which the 2 amino substituents are selected from alkyl, aryl or arylalkyl, alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, substituted sulfonamido, nitro, cyano, carboxy, carbamyl, substituted carbamyl (e.g., CONHalkyl, CONHaryl, CONHarylalkyl, or cases where there are two substituents on the nitrogen are selected from alkyl, aryl or arylalkyl), alkoxycarbonyl, aryl, substituted aryl, guanidino, heterocyclyl, (e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl, and the like), and substituted heterocyclyl. Where a substituent is further substituted it may be with alkyl, alkoxy, aryl or arylalkyl.

"Halogen" or "halo" refers to fluorine, chlorine, bromine, andiodine.

"Aryl" refers to monocyclic or bicyclic aromatic hydrocarbon groups having 6 to 12 carbon atoms in the ring, such as phenyl, naphthyl, biphenyl, and diphenyl, each of which may be substituted.

"Aaryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", and "arylalkylsulfonyl" refer to an aryl or substituted aryl bonded to oxygen; amino; alkylamino; thio; alkanoylamino; sulfonyl; alkoxy; sulfinyl; heteroaryl or substituted heteroaryl; alkylthio; carbonyl; alkenyl; or alkylsulfonyl, respectively.

"Arylsulfonylaminocarbonyl" refers to an arylsulfonyl bonded to an aminocarbonyl.

"Aryloxyalkyl", "aryloxycarbonyl", or "aryloxyaryl" refer to an aryloxy bonded to an alkyl or substituted alkyl; a carbonyl; or an aryl or substituted aryl, respectively.

"Arylalkyl" refers to an alkyl or substituted alkyl in which at least one of the hydrogen atoms bonded to at least one of the carbon atoms is replaced with an aryl or substituted aryl. Typical arylalkyls include, but are not limited to benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

"Arylalkyloxy" refers to an arylalkyl bonded through an oxygen linkage (—O-arylalkyl).

"Substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkylsulfonyl, sulfonamido, aryloxy, and the like. The substituent may be further substituted by hydroxy, halo, alkyl, alkoxy, alkenyl, alkynyl, aryl, or arylalkyl.

"Heteroaryl" refers to an optionally substituted aromatic group which is a 4 to 7 membered monocyclic, a 7 to 11 membered bicyclic, or a 10 to 15 membered tricyclic ring system, which has at least one heteroatom and at least one carbon atom-containing ring, for example, pyridine, tetrazole, indazole.

"Alkenyl" refers to straight or branched chain hydrocarbon groups of 2 to 20 carbon atoms, preferably 2 to 15 carbon atoms, and most preferably 2 to 8 carbon atoms, having one to four double bonds.

"Substituted alkenyl" refers to an alkenyl group substituted by one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl, and the like.

"Alkynyl" refers to straight or branched chain hydrocarbon groups of 2 to 20 carbon atoms, preferably 2 to 15 carbon atoms, and most preferably 2 to 8 carbon atoms, having one to four triple bonds.

"Substituted alkynyl" refers to an alkynyl group substituted by halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiaZolyl, pyrrolidyl, pyridyl, pyrimidyl and the like.

"Alkylidene" refers to an alkylene group consisting of at least two carbon atoms and at least one carbon-carbon double bond. Substituents on this group include those in the definition of "substituted alkyl".

"Cycloalkyl" refers to an optionally substituted, saturated cyclic hydrocarbon ring systems, preferably containing 1 to 3 rings and 3 to 7 carbons per ring which may be further fused with an unsaturated C3-C7 carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups or one or more groups described herein as alkyl substituents.

"Heterocycle", "heterocyclic", and "heterocyclyl" refer to an optionally substituted, fully saturated or unsaturated, aromatic or non-aromatic cyclic group, which is a 4 to 7 membered monocyclic, 7 to 11 membered bicyclic, or 10 to 15 membered tricyclic ring system which has at least one heteroatom in at least one carbon atom-containing ring. Each ring of the heterocyclic group containing a heteroatom may have 1, 2, or 3 heteroatoms selected from nitrogen, oxygen, and sulfur, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinylsulfone, 1,3-dioxolane, tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl]furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzopyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like. Exemplary substituents include one or more alkyl or arylalkyl groups as described supra or one or more groups described supra as alkyl substituents and smaller heterocyclyls, such as, epoxides and aziridines.

"Carbocyclic ring" or "carbocyclyl" refers to stable, saturated, partially saturated or unsaturated, mono or bicyclic hydrocarbon rings that contain 3-12 atoms. This includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl, and tetrahydronaphthyl.

"Optionally substituted" as it refers to "carbocyclic ring" or "carbocyclyl" indicates that the carbocyclic ring may be substituted at one or more substitutable ring positions by one or more groups independently selected from alkyl (preferably lower alkyl), alkoxy (preferably lower alkoxy), nitro, monoalkylamino (preferably lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably lower alkoxycarbonyl), alkylcarbonyloxy (preferably lower alkylcarbonyloxy) and aryl (preferably phenyl), said aryl being optionally substituted by halo, lower alkyl and lower alkoxy groups.

"Heteroatoms" includes oxygen, sulfur, and nitrogen.

"Alkylsulfone" refers to —$R^kS(=O)_2R^k$, wherein $R^k$ is alkyl or substituted alkyl.

"Oxo" refers to the divalent radical =O.

"Carbamate" refers to —$OC(=O)NH_2$.

"Amide" refers to —$C(=O)NH_2$.

"Sulfonamide" refers to —$SO_2NH_2$.

"Substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide refers to —$C(=O)NR'''R''$ wherein $R'''$ and $R''$ are independently selected from H, alkyl, substituted alkyl, alkenyl, substituted alkenyl, cycloalkyl, and substituted cycloalkyl, provided at least one of $R'''$ or $R''$ is a substituted moiety.

Substituted sulfonamide refers to the group —$SO_2NR^oR^p$, wherein $R^o$ and $R^p$ are independently selected from alkyl, substituted alkyl, alkenyl, substituted alkenyl, cycloalkyl, and substituted cycloalkyl, provided at least one of $R^o$ and $R^p$ is a substituted moiety.

Substituted carbamate refers to —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

"Ureido" refers to the group —$NHC(=O)NH_2$.

"Cyano" refers to the group —CN.

"Cycloalkylalkyl" or "cycloalkylalkoxy" refer to a cycloalkyl or substituted cycloalkyl bonded to an alkyl or substituted alkyl; or an alkoxy, respectively.

"Nitro" refers to the group —$N(O)_2$—

"Thio" refers to the group —SH.

"Alkylthio" refers to the group —$SR^s$ where $R^s$ is an alkyl, substituted alkyl, cycloalkyl, or substituted cycloalkyl.

"Thioalkyl" refers to the group —$R^rS$ where $R^r$ is an alkyl, substituted alkyl, cycloalkyl, or substituted cycloalkyl.

"Alkylsulfonyl" refers to the group —$S(=O)_2R^u$ where $R^u$ is an alkyl, substituted alkyl, cycloalkyl, or substituted cycloalkyl.

"Alkylsulfinyl" refers to the group —$S(=O)R^v$ where $R^v$ is an alkyl, substituted alkyl, cycloalkyl, or substituted cycloalkyl.

"Carboxy" refers to the group —$C(=O)OH$.

"Carboxyalkoxy" or "alkoxycarbonylalkoxy" refer to a carboxy, or an alkoxycarbonyl, respectively, bonded to an alkoxy.

"Alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

"Arylalkoxycarbonyl" refers to an aryl or substituted aryl bonded to an alkoxycarbonyl.

"Alkylcarbonyloxy" or "arylcarbonyloxy" refer to the group —$OC(=O)R^x$ where $R^x$ is an alkyl or substituted alkyl, or an aryl or substituted aryl, respectively.

"Carbamoyl" refers to the groups —$OC(=O)NH_2$, —$OC(=O)NHR^x$ and/or —$C(=O)NR^yR^z$, wherein $R^y$ and $R^z$ are independently selected from alkyl and substituted alkyl.

The group —$NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

"Carbonyl" refers to a $C(=O)$.

"Alkylcarbonyl", "aminocarbonyl", "alkylaminocarbonyl", "aminoalkylcarbonyl", or "arylaminocarbonyl" refer to alkyl, substituted alkyl, ammo; alkylamino, substituted alkylamino, aminoalkyl, substituted aminoalkyl, or arylamino, respectively, bonded to a carbonyl.

"Aminocarbonylaryl" or "aminocarbonylalkyl" refer to an aminocarbonyl bonded to an aryl or substituted aryl; or an alkyl or substituted alkyl, respectively.

"Sulfonyl" refers to the group $S(=O)_2$.

"Sulfinyl" refers to the group $S(=O)$.

"Carboxyalkyl" refers to alkyl or substituted alkyl bonded to a carboxy.

The compounds of formula I may form salts. Pharmaceutically acceptable (i.e. non-toxic, physiologically acceptable) salts are preferred, although other salts are also useful, e.g., in isolating or purifying the compounds. The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed by methods known to those skilled in the art.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, y-hydroxybutyrates, glycolates, tartrates, and mandelates.

The compounds for formula I may form salts with a variety of organic and inorganic acids. Such salts include those formed with hydrogen chloride, hydrogen bromide, methane sulfonic acid, sulfuric acid, acetic acid, trifluoroacetic acid, oxalic acid, maleic acid, benzenesulfonic acid, toluene sulfonic acid and various others (e.g., nitrates, phosphates, borates, tartrates, citrates, succinates, benzoates, ascorbates, salicylates, and the like). Such salts can be formed by methods known to those skilled in the art. In addition, zwitterions ("inner salts") may be formed.

All stereoisomers of the compounds are also contemplated as anti-NTCP agents, either in admixture or in pure or substantially pure form. The definition of compounds thus embraces all possible stereoisomers and their mixtures, in particular the racemic forms and the isolated optical isomers having the specified activity. The racemic forms can be resolved by physical methods, such as, fractional crystallization, separation or crystallization of diastereomeric derivatives, or separation by chiral column chromatography. The individual optical isomers can be obtained from the racemates from the conventional methods, such as, for example, salt formation with an optically active acid followed by crystallization.

Compounds of formula I may also be administered in prodrug forms. "Prodrugs" are intended to include any covalently bonded carriers that release an active parent drug in vivo when such prodrug is administered to a mammalian subject. Prodrugs are prepared by modifying functional groups present in the compound in such a way that the modifications are cleaved, either in routine manipulation or in vivo to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include acetate, formate, and benzoate derivatives of alcohol and amine functional groups in the compounds of the invention. Various forms of prodrugs are well known in the art. For example, see Design of Prodrugs, edited by H. Bundgaard, (Elsevier, 1985) and Methods in Enzymology, Vol. 112, pp. 309-396, edited by K. Widder, et al. (Academic Press, 1985).

Solvates (e.g., hydrates) of the compounds of formula I are also included as anti-NTCP agents. Methods of solvation are known in the art.

The compounds of formula I may be administered in a dosage range of about 0.05 to 200 mg/kg/day, preferably less than 100 mg/kg/day, in a single dose or in 2 to 4 divided doses.

Combination of NTCP Inhibitors

According to the invention, one or more NTCP inhibitors may be administered to the subject. One of the NTCP inhibitors may be an pre-S1 peptide inhibitor. Two or more NTCP inhibitors may be administered sequentially. For example, one NTCP inhibitor such as pre-S1 peptide inhibitor may be administered for at least one cycle or a course comprising one or more cycles (such as 2, 3, 4, 5, 6, 7, 8, 9 or 10 cycles) followed by the administration of a further NTCP inhibitor for at least one cycle or a course comprising one or more cycles (such as 2, 3, 4, 5, 6, 7, 8, 9 or 10 cycles). The duration of one cycle may be 1, 2, 3, 4, 5, 6, 7, 8, 9, 10, 11, or 12 weeks. The duration of one cycle may be at least 1, 2, 3, 4, 5, 6, 7, 8, 9, 10, 11, or 12 weeks. The duration of one course may be 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3 years, or 4 years or longer.

In the uses and methods of the invention, two or more NTCP inhibitors may be administered concomitantly/concurrently. According to this administration schedule, the administration of two or more NTCP inhibitors timely overlaps. The duration of the administration of two or more NTCP inhibitors may be identical or essentially identical. For example, two NTCP inhibitors, one of which is a pre-S1 peptide inhibitor may be administered for at least one cycle or a course comprising one or more cycles (such as 2, 3, 4, 5, 6, 7, 8, 9 or 10 cycles). The duration of one cycle may be 1, 2, 3, 4, 5, 6, 7, 8, 9, 10, 11, or 12 weeks. The duration of one cycle may be at least 1, 2, 3, 4, 5, 6, 7, 8, 9, 10, 11, or 12 weeks. The duration of one course may be 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3 years, or 4 years. For example, a 24 weeks course of Myrcludex B (e.g., 5 mg daily) may be administered at the same time as a 24 weeks course of another NTCP inhibitor such as a compound of formula I or a modified bile salt. In this administration scheme, Myrcludex B may be administered daily, whereas the other NTCP inhibitor may be administered weekly. In this administration schedule, two NTCP inhibitors may be administered simultaneously, for example at essentially the same time or in a single composition.

In the uses and methods of the invention, an NTCP inhibitor maybe delivered by various delivery routes, depending on the type of ingredient. Administration routs include enteral route (e.g., orally and rectally), parenteral route (e.g. intravenously, intramuscularly, subcutaneously intraperitonealy) and topically. Preferably, pre-S1 peptide inhibitor is delivered subcutaneously.

Pharmaceutical Compositions

The NTCP inhibitors for use according to the invention may be comprised in a pharmaceutical composition. Pharmaceutical compositions for use according to the invention may be in a form suitable for oral use, for example, as tablets, troches, lozenges, aqueous or oily suspensions, dispersible powders or granules, emulsions, hard or soft capsules, syrups, or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with a water soluble carrier such as polyethyleneglycol or an oil medium, such as peanut oil, liquid parafin, or olive oil.

The pharmaceutical compositions may be in the form of sterile injectable aqueous solutions. Among the acceptable vehicles and solvents that may be employed are water, Ringer's solution, and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized.

The pharmaceutical compositions may be in the form of a sterile injectable aqueous or oleaginous suspension for intramuscular and subcutaneous administration. This suspension may be formulated according to the known art using suitable dispersing or wetting agents and suspending agents.

Diseases to be Treated

The invention is directed to the treatment of primary biliary cirrhosis atherosclerosis, and NRLP3 inflammasome-associated diseases. NRLP3 inflammasome-associated diseases include, but are not limited to type-2 diabetes, atherosclerosis, gout, Alzheimer's disease and NASH.

Treatment Regiments

When an NTCP inhibitor for use according to the invention is administered into a human subject, the daily dosage will normally be determined by the prescribing physician with the dosage generally varying according to the age, weight, sex and response of the individual patient, as well as the severity of the patient's symptoms. Exemplary doses for some NTCP inhibitors for use according to the invention are described herein.

Within the use of the invention, an NTCP inhibitor may be provided in a therapeutically effective amount. The term "therapeutically effective amount" or "effective amount" commonly refers to an amount of a therapeutic agent that when administered alone or in combination with an additional therapeutic agent to a cell, tissue, or subject is effective to prevent or ameliorate the infection or the progression of the infection or an associated disease associated with the infection. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions.

When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In particular, an effective amount is an amount that inhibits or reduces viral entry into a cell.

In the uses and methods of the invention, the dose of each active ingredient may be adjusted according to the treatment progression and/or side effects the patient develops during the treatment.

The invention explicitly includes specific active ingredients (as NTCP inhibitors) and the administration schedules as described in the examples of the application.

The invention will be illustrated by reference to the following non-limiting examples.

Certain Items

The application discloses inter alia certain items:

1. An inhibitor of Na+-taurocholate cotransporting polypeptide (NTCP) for use in a method of treatment of atherosclerosis, primary biliary cirrhosis, or an NRLP3 inflammasome-associated disease in a subject.

2. The NTCP inhibitor for use of item 1, wherein the NTCP inhibitor is a pre-S1 peptide inhibitor, wherein the pre-S1 peptide inhibitor comprises a peptide comprising amino acid sequence NPLGFX$_0$P (SEQ ID NO: 15), and wherein X$_0$ is any amino acid, preferably F or L, more preferably F.

3. The NTCP inhibitor for use of item 2, wherein the pre-S1 peptide inhibitor further comprises an N-terminal sequence of at least 4 amino acids at the N-terminus of NPLGFX$_0$P (SEQ ID NO: 15).

4. The NTCP inhibitor for use of item 3, wherein the N-terminal sequence consists of 4, 5, 6, 7, 8, 9, 10, 11, 12, 13, 14, 15, 16, 17, 18, or 19 amino acids, or wherein the N-terminal sequence consists of 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19 amino acids.

5. The NTCP inhibitor for use of item 3 or 4, wherein at least one amino acid of the N-terminal sequence has an amino group in a side chain.

6. The NTCP inhibitor for use of item 5, wherein the at least one amino acid of the N-terminal sequence is/are selected from lysine, α-amino glycine, α,γ-diaminobutyric acid, ornithine, α,ß-diaminopropionic acid, preferably lysine.

7. The NTCP inhibitor for use of item 5 or 6, wherein the at least one amino acid of the N-terminal sequence is/are located at the N-terminus of the N-terminal sequence.

8. The NTCP inhibitor for use of items 5-7, wherein the at least one amino acid of the N-terminal sequence is 1, 2, 3, 4, 5, 6, 7, 8, 9, 10 or 11 amino acids, or wherein the at least one amino acid of the N-terminal sequence is 1 to 3, 1 to 4, 1 to 5, 1 to 6, 1 to 7, 1 to 8, 1 to 9, or 1 to 10 amino acids.

9. The NTCP inhibitor for use of items 3-8, wherein the N-terminal sequence comprises amino acid sequence NX$_1$SX$_2$X$_3$ (SEQ ID NO: 16), wherein X$_1$, X$_2$ and X$_3$ is any amino acid.

10. The NTCP inhibitor for use of item 9, wherein in NX$_1$SX$_2$X$_3$ (SEQ ID NO: 16):
X$_1$ is L, I or Q, preferably L;
X$_2$ is T, V, A or is absent, preferably T or V, more preferably T; and/or
X$_3$ of is P, S, T or F, preferably P or S, more preferably S.

11. The NTCP inhibitor for use of item 9 or 10, wherein amino acid sequence NX$_1$SX$_2$X$_3$ (SEQ ID NO: 16) is directly attached to the N-terminus of NPLGFX$_0$P (SEQ ID NO: 15).

12. The NTCP inhibitor for use of items 2-11, wherein of the pre-S1 peptide inhibitor comprises amino acid sequence NX$_1$SX$_2$X$_3$NPLGFX$_0$P (SEQ ID NO: 17), wherein
X$_0$ is any amino acid,
X$_1$ is L, I or Q, preferably L;
X$_2$ is T, V, A or is absent, preferably T or V, more preferably T; and
X$_3$ of is P, S, T or F, preferably P or S, more preferably S.

13. The NTCP inhibitor for use of items 2-12, wherein the pre-S1 peptide inhibitor further comprises a C-terminal sequence of at least 1 amino acid at the C-terminus of NPLGFX$_0$P (SEQ ID NO: 15).

14. The NTCP inhibitor for use of item 13, wherein the C-terminal sequence consists of 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92 or 93 amino acids, or wherein the C-terminal sequence consists of 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, 1 to 30, 1 to 31, 1 to 32, 1 to 33, 1 to 34, or 1 to 35 amino acids.
15. The NTCP inhibitor for use of item 13 or 14, wherein the C-terminal sequence comprises amino acid sequence $X_4$HQLDP (SEQ ID NO: 18), wherein $X_4$ is any amino acid.
16. The NTCP inhibitor for use of item 15, wherein $X_4$ is D, E or S, preferably D or E, more preferably D.
17. The NTCP inhibitor for use of items 15 or 16, wherein amino acid sequence $X_4$HQLDP (SEQ ID NO: 18) is directly attached to the C-terminus of NPLGF$X_0$P (SEQ ID NO: 15).
18. The NTCP inhibitor for use of items 2-17, wherein of the pre-S1 peptide inhibitor comprises amino acid sequence NPLGF$X_0$P$X_4$HQLDP (SEQ ID NO: 19), wherein
   $X_0$ is any amino acid; and
   $X_4$ is D, E or S, preferably D or E, more preferably D.
19. The NTCP inhibitor for use of items 2-18, wherein of the pre-S1 peptide inhibitor comprises amino acid sequence N$X_1$S$X_2$$X_3$NPLGF$X_0$P$X_4$HQLDP (SEQ ID NO: 20), wherein
   $X_0$ is any amino acid, preferably F or L, more preferably F;
   $X_1$ is L, I or Q, preferably L;
   $X_2$ is T, V, A or is absent, preferably T or V, more preferably T;
   $X_3$ of is P, S, T or F, preferably P or S, more preferably S; and
   $X_4$ is D, E or S, preferably D or E, more preferably D.
20. The NTCP inhibitor for use of items 2-19, wherein of the pre-S1 peptide inhibitor comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids.
21. The NTCP inhibitor for use of items 2-20, wherein of the pre-S1 peptide inhibitor comprises a pre-S1 peptide of an HBV virus, or a functional fragment thereof, wherein the function is preferably binding to NTCP, inhibition of NTCP, or reduction of NTCP activity.
22. The NTCP inhibitor for use of item 21, wherein the pre-S1 peptide inhibitor comprises or consists of:
   at least amino acids 9 to 15, 8 to 15, 7 to 15, 6 to 15, 5 to 15, 4 to 15, 3 to 15, 2 to 15 of a pre-S1 peptide of an HBV virus;
   at least amino acids 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 9 to 31, 9 to 32, 9 to 33, 9 to 34, 9 to 35, 9 to 36, 9 to 37, 9 to 38, 9 to 39, 9 to 40, 9 to 41, 9 to 42, 9 to 43, 9 to 44, 9 to 45, 9 to 46, 9 to 47, 9 to 48 of a pre-S1 peptide of an HBV virus;
   at least amino acids 8 to 16, 7 to 17, 6 to 18, 5 to 19, 4 to 20, 3 to 21, or 2 to 22 of a pre-S1 peptide of an HBV virus;
   at least amino acids 2 to 15, 2 to 16, 2 to 17, 2 to 18, 2 to 19, 2 to 19, 2 to 20, 2 to 21, 2 to 22, 2 to 23, 2 to 24, 2 to 252 to 26, 2 to 27, 2 to 28, 2 to 29, 2 to 30, 2 to 31, 2 to 32, 2 to 33, 2 to 34, 2 to 35, 2 to 36, 2 to 37, 2 to 38, 2 to 39, 2 to 40, 2 to 41, 2 to 42, 2 to 43, 2 to 44, 2 to 45, 2 to 46, 2 to 47, or 2 to 48 of a pre-S1 peptide of an HBV virus;
   at least amino acids 9 to 15 and 16 to 20 of a pre-S1 peptide of an HBV virus;
   at least amino acids 2 to 8 and 9 to 15 of a pre-S1 peptide of an HBV virus;
   at least amino acids 2 to 8, 9 to 15 and 16 to 20 of a pre-S1 peptide of an HBV virus;
   at least amino acids 9 to 15 and 34 to 48 of a pre-S1 peptide of an HBV virus;
   at least amino acids 9 to 15, 16 to 20 and 34 to 48 of a pre-S1 peptide of an HBV virus;
   at least amino acids 2 to 8, 9 to 15 and 34 to 48 of a pre-S1 peptide of an HBV virus;
   at least amino acids 2 to 8, 9 to 15, 16 to 20 and 34 to 48 of a pre-S1 peptide of an HBV virus;
   at least amino acids 2 to 48 of a pre-S1 peptide of an HBV virus or a portion thereof of at least 15 amino acids;
   amino acids 2 to 48 of a pre-S1 peptide of an HBV virus; or
   a sequence having at least 50%, 55%, 60%, 65%, 70%, 75%, 80%, 85%, 90%, or 95% identity with any of the above sequences.
23. The NTCP inhibitor for use of item 21 or 22, wherein the HBV virus is HBV strain alpha1, HBV strain LSH, woodchuck HBV, Woolly Monkey HBV (WMHBV), orangutan HBV, chimpanzee HBV, gorilla HBV, human HBV, HBV subtype AD, ADR, ADW, ADYW, AR or AYW, or HBV genotype A, B, C, D, E, F, G or H.
24. The NTCP inhibitor for use of items 2-23, wherein the pre-S1 peptide inhibitor comprises or consists of amino acid sequence

```
                                          (SEQ ID NO: 1)
(-11)-M GGWSS TPRKG MGTNL SVPNP LGFFP DHQLD PAFRA

NSNNP DWDFN PNKDH WPEAN KVG-48

(SEQ ID NO: 2)
(-11)-M GGWSS KPRKG MGTNL SVPNP LGFFP DHQLD PAFGA

NSNNP DWDFN PVKDD WPAAN QVG-48

(SEQ ID NO: 3)
(-11)-M GGWSS KPRKG MGTNL SVPNP LGFFP DHQLD PAFKA

NSENP DWDLN PHKDN WPDAN KVG-48

(SEQ ID NO: 4)
(-11)-M GGWSS KPRQG MGTNL SVPNP LGFFP DHQLD PAFGA

NSNNP DWDFN PNKDH WPEAN QVG-48

(SEQ ID NO: 5)
1-MGQNL STSNP LGFFP DHQLD PAFRA NTANP DWDFN PNKDT

WPDAN KVG-48

SEQ ID NO: 6)
(-10)-MGLSW TVPLE WGKNI STTNP LGFFP DHQLD PAFRA

NTRNP DWDHN PNKDH WTEAN KVG-48

(SEQ ID NO: 7)
(-11)-M GAPLS TTRRG MGQNL SVPNP LGFFP DHQLD PLFRA

NSSSP DWDFN TNKDS WPMAN KVG-48

(SEQ ID NO: 8)
(-10)-MGLSW TVPLE WGKNL SASNP LGFLP DHQLD PAFRA

NTNNP DWDFN PKKDP WPEAN KVG-48
```

-continued

```
                                           (SEQ ID NO: 9)
(-11)-M GAPLS TARRG MGQNL SVPNP LGFFP DHQLD PLFRA

NSSSP DWDF TNKDN WPMAN KVG-48

(SEQ ID NO: 10)
1-MGLNQ STFNP LGFFP SHQLD PLFKA NAGSA DWDKN PNKDP

WPQAH DTA (SEQ ID NO: 11)
(-11)-M GGWSS KPRQG MGTNL SVPNP LGFFP DHQLD PAFGA

NSNNP DWDFN PNKDH WPEAN KVG-48,
``` or
- a fragment thereof of at least 15 amino acids, or
- a sequence having at least 50%, 55%, 60%, 65%, 70%, 75%, 80%, 85%, 90%, or 95% identity with any of the above sequences.

25. The NTCP inhibitor for use of items 2-24, wherein the pre-S1 peptide inhibitor comprises or consists of amino acid sequence

```
                                           (SEQ ID NO: 12)
GTNL SVPNP LGFFP DHQLD PAFRA NSNNP DWDFN PNKDH

WPEAN KVG;

(SEQ ID NO: 13)
GTNL SVPNP LGFFP DHQLD PAFGA NSNNP DWDFN PNKDH

WPEAN KVG;

(SEQ ID NO: 14)
GTNL SVPNP LGFFP DHQLD PAFGA NSNNP DWDFN PNKDH

WPEAN QVG;
``` or
- a sequence having at least 50%, 55%, 60%, 65%, 70%, 75%, 80%, 85%, 90%, or 95% identity with any of the above sequences.

26. The NTCP inhibitor for use of items 2-25, wherein the pre-S1 peptide inhibitor is modified by at least one hydrophobic moiety at the N-terminus or in 1, 2, 3, or 4 amino acids proximity to the N-terminus.

27. The NTCP inhibitor for use of item 26, wherein the hydrophobic moiety modification is acylation.

28. The NTCP inhibitor for use of item 27, wherein the acylation is an acylation with carboxylic acids, fatty acids and amino acids with lipophilic side chains.

29. The NTCP inhibitor for use of item 28, wherein the fatty acids are saturated or unsaturated fatty acids, branched or unbranched fatty acids, preferably with 8 to 22 carbon atoms (C8 to C22).

30. The NTCP inhibitor for use of item 27-29, wherein the acylation is an acylation with myristoyl (C14), palmitoyl (C16), or stearoyl (C18).

31. The NTCP inhibitor for use of item 27-30, wherein the acylation is an acylation with myristoyl.

32. The NTCP inhibitor for use of item 26, wherein the hydrophobic moiety modification is addition of a hydrophobic moiety.

33. The NTCP inhibitor for use of item 32, wherein the hydrophobic moiety is cholesterol, derivatives of cholesterol, phospholipids, glycolipids, glycerol esters, steroids, ceramids, isoprene derivatives, adamantane, farnesol, aliphatic groups, polyaromatic compounds, oleic acid, bile salts or bile salt conjugates, preferably oleic acid, cholesterol, bile salts or bile salt conjugates.

34. The NTCP inhibitor for use of item 32 or 33, wherein the hydrophobic moiety is attached by covalent binding, preferably via carbamate, amide, ether, or disulfide.

35. The NTCP inhibitor for use of items 2-34, wherein the pre-S1 peptide inhibitor is modified by at least one protective moiety at the C-terminus or in 1, 2, 3, or 4 amino acids proximity to the C-terminus, wherein the protective moiety protects the pre-S1 peptide inhibitor from degradation.

36. The NTCP inhibitor for use of item 35, wherein the protective moiety is an amide, a D-amino acid, a modified amino acid, a cyclic amino acid, an albumin, a glycan, or a natural or synthetic polymer, preferably PEG.

37. The NTCP inhibitor for use of item 35 or 36, wherein the protective moiety is amide.

38. The NTCP inhibitor for use of items 35 to 37, wherein the protective moiety is attached via a linker.

39. The NTCP inhibitor for use of item 39, wherein the linker is polyalanine, polyglycin, carbohydrates, or $(CH_2)_n$ groups, wherein n is 1 or more.

40. The NTCP inhibitor for use of items 2-39, wherein the pre-S1 peptide inhibitor consists of amino acid sequence 2 to 48 of genotype C preS1 peptide which is modified at the N-terminus by myristoylation and further modified at the C-terminus with amide.

41. The NTCP inhibitor for use of items 2-40, wherein the pre-S1 peptide inhibitor is

```
Myr-GTNLSVPNPLGFFPDHQLDPAFGANSNNPDWDFNPNKDHWPEA

NKVG-amide.
```

42. The composition or combination of items 2-40, wherein the pre-S1 peptide inhibitor is N-Myristoyl-glycyl-L-threonyl-L-asparaainyl-L-leucyl-L-seryl-L-valyl-L-prolyl-L-asparaginyl-L-prolyl-L-leucyl -glycyl-L-phenylalanyl-L-phenylalanyl-L-prolyl-L-aspartyl-L-histidyl-L-glutaminyl-L-leucyl-L-aspartyl-L-prolyl-L-alartyl-L -phenylalanyl-glycyl-L-alanyl-L-asparaginyl-L-seryl-L-asparaginyl-L-asparaginyl-L-prolyl-L-aspartyl-L-tryptophanyl-L-aspartyl-L -phenylalanyl-L-asparaginyl-L-prolyl-L-asparaginyl-L-lysyl-L-aspartyl-L-histidyl-L -tryptophanyl-L-prolyl-L-giutantyl-L-alanyl-L-asparaginyl-L-lysyl-L-valyl-glycinamide, or an acetate salt thereof.

43. The NTCP inhibitor for use of items 2-42, wherein the method comprises administering the pre-S1 peptide inhibitor:
- at a dose such that the concentration of the pre-S1 peptide inhibitor at the NTCP site, i.e., in hepatocytes, is equal or above a Ki of about 1 to 10 nM;
- at a daily dose of between 0.1 mg and 50 mg, 0.5 mg and 20 mg per day, 1 mg to 15 mg, 1 mg to 10 mg, 1 mg to 5 mg, preferably 2 mg, 3 mg, 4 mg, 5 mg, 6 mg, 7 mg, 8 mg, 9 mg or 10 mg per day; or
- at a daily dosage of between about 0.0014 mg/kg body weight and about 0.7 mg/kg body weight, preferably between about 0.014 mg/kg body weight to about 0.28 mg/kg body weight (1 mg to 20 mg).

44. The NTCP inhibitor for use of items 2-43, wherein the method comprises administering the pre-S1 peptide inhibitor for 2 weeks, 3, weeks, 4 weeks, 5 weeks, 6 weeks, 12 weeks, 24 weeks, 36 weeks, 48 weeks, 60 weeks, 1 year, 1.1 years, 1.2 years, 1.3 years, 1.4 years, 1.5 years, 1.6 years, 1.7 years, 1.8 years, 1.8 years, 1.9 years, or 2.0 years, or 3 years, or 4 years or longer.

45. The NTCP inhibitor for use of items 2-44, wherein the method comprises administering the pre-S1 peptide inhibitor at a dose of 2 mg daily or 5 mg daily for 24 weeks or 48 weeks.

46. The NTCP inhibitor for use of items 2-45, wherein the method comprises administering the pre-S1 peptide inhibitor subcutaneously, intravenously, orally, nasally, intramuscularly, transdermally, by inhalation or suppository, preferably intravenously or subcutaneously.

47. The NTCP inhibitor for use of item 2-46, wherein the method comprises administering the pre-S1 inhibitor and a further NTCP inhibitor.

48. The NTCP inhibitor for use of items 1-47, wherein the subject is a human.

49. The NTCP inhibitor for use of items 1-48, wherein the atherosclerosis is at a stage of unstable atherosclerotic plaques.

50. The NTCP inhibitor for use of items 1-49, wherein the method results in the reduction, resolution or elimination of atherosclerotic plaques.

51. The NTCP inhibitor for use of items 1-48, wherein the method results in the reduction, or elimination of symptoms of primary biliary cirrhosis.

52. The NTCP inhibitor for use of item 51, wherein the method results in normalization of biochemical parameters and decrease in inflammation and fibrosis progression.

53. The NTCP inhibitor for use of items 1-48, wherein the NRLP3 inflammasome-associated disease is type-2 diabetes, atherosclerosis, gout, Alzheimer's disease and NASH.

54. The NTCP inhibitor for use of item 53, wherein the method results in normalization of biochemical parameters and improvement of disease progression.

55. Method of treatment of atherosclerosis, primary biliary cirrhosis, or an NRLP3 inflammasome-associated disease in a subject, comprising administering to the subject an NTCP inhibitor.

56. The method of item 55, wherein the NTCP inhibitor is as a pre-S1 inhibitor as defined in items 2 to 42.

57. The method of item 55 or 56, wherein the method is as defined in items 43 to 47.

58. The method of items 55-57, wherein the subject is a human.

59. The method of items 55-58, wherein the diseases are as defined in items 49 to 54.

EXAMPLES

Example 1: Study of an HTCP Inhibitor in APO-E Knock-Out Mice

Objective:

The objective of this study is the evaluation of the effect of an HTCP inhibitor Myrcludex B at various doses on physiology and atherosclerotic lesion development in APO-E knockout mice, an animal model that closely resembles the human atherosclerotic condition.

Methodology:
Test weeks 1-8:
Randomization and allocation to 4 test groups:

| Groups | | Number of animals | |
|---|---|---|---|
| | | Male | Female |
| 1 Control | 0 | 5 | 5 |
| 2 Test Item | Dose level 1 | 5 | 5 |

Administration: Daily s.c. injection
Special housing conditions:

| Diet | Standard diet for all study groups |
|---|---|

Parameters to be determined:

| Clinical signs | Daily |
|---|---|
| Mortality/Morbidity | Daily |
| Body weight | At start, weekly thereafter, at interim dissection |
| Food consumption | Weekly (mean values) |
| Clinical biochemistry | All animals |
| | At dissection |
| | Using the Konelab 30i instrument |
| | Parameters: total bile acid LDL, HDL, VLDL, cholesterol |
| Dissection/Necropsy | All animals |
| | Dissection incl. macroscopic inspection |
| | Quantitative determination of atherosclerotic lesions in the aorta regions |
| | Storage of terminal plasma sample (≤−20° C.) for further investigation |
| Report | Available approximately 4-6 weeks after study termination. |

Results: Myrcludex B was well tolerated.

Example 2: Study of an HTCP Inhibitor in LDL Receptor Knock-Out Mice

Objective:

The objective of this 23 weeks study is the evaluation of the effect of an HTCP inhibitor Myrcludex B at various doses on physiology and atherosclerotic lesion development in LDL receptor-knockout mice (LDLRKO), an animal model that closely resembles the human atherosclerotic condition.

Methodology:
16 male and 6 female LDLRKO mice
8 weeks on high calorie diet
Sacrifice of 4 males and 4 females
Randomization of remaining animals to 4 groups
15 weeks on standard diet and daily s.c. Myrcludex B treatment starting on week 9
Species/Strain: Mouse LDLR Knock-Out/B6.12957-Ldlrtm1Her/J
Supplier: The Jackson Laboratory. USA
Test weeks 1-8:

| Groups | Number of animals |
|---|---|
| 1 Pool | 16 male + 16 female |

| Diet | High calorie diet in weeks 1-8 |

Parameters to be determined:

| | |
|---|---|
| Clinical signs | Daily |
| Mortality/Morbidity | Daily |
| Body weight | At start, weekly thereafter, at interim dissection |
| Food consumption | Weekly (mean values) |
| Clinical biochemistry | All animals |
| | Pre-dose |
| | At interim sacrifice after 8 weeks |
| | Using the Konelab 30i instrument |
| | Parameters: total bile acid LDL, HDL, VLDL, cholesterol |
| Dissection/Necropsy | 8 (4 m + 4 f) randomly selected animals |
| | Dissection incl. macroscopic inspection |
| | Quantitative determination of atherosclerotic lesions in the aorta regions |
| | Storage of terminal plasma sample (≤−20° C.) for further investigation |
| Interim Report | Available approximately within 4 weeks after interim |

Test weeks 9-23:
Randomization and allocation to 4 test groups:

| | | Number of animals | |
|---|---|---|---|
| Groups | | Male | Female |
| 1 Control | 0 | 5 | 5 |
| 2 Test Item | Dose level 1 | 5 | 5 |

Administration: Daily s.c. injection starting in test week 9
Special housing conditions:

| Diet | Standard diet for all study groups |

Parameters to be determined:

| | |
|---|---|
| Clinical signs | Daily |
| Mortality/Morbidity | Daily |
| Body weight | At start, weekly thereafter, at interim dissection |
| Food consumption | Weekly (mean values) |
| Clinical biochemistry | All animals |
| | At dissection |
| | Using the Konelab 30i instrument |
| | Parameters: total bile acid LDL, HDL, VLDL, cholesterol |
| Dissection/Necropsy | All animals |
| | Dissection incl. macroscopic inspection |
| | Quantitative determination of atherosclerotic lesions in the aorta regions |
| | Storage of terminal plasma sample (≤−20° C.) for further investigation |
| Report | Available approximately 4-6 weeks after study termination. |

Results: Myrcludex B was well tolerated.

Example 3: Pilot Clinical Trial in Patients with Dyslipidaemia with a HTCP Inhibitor Mycludex B Objective:
The objective of the clinical trial is the evaluation of safety and tolerability, as well as efficacy of Myrcludex B in patients with dyslipidaemia.
Methodology:
20 patients with dyslipidaemia
8 weeks of Myrcludex B, 10 mg daily
Endothelial function examination, lipid panel and further biomarkers: assay of macrophage cholesterol efflux and ATP-binding cassette transporter genes ABCA1 and ABCG1.
Results:
Myrcludex B was well tolerated.

Example 4: Phase 2 Clinical Trial of PBC Treatment with a HTCP Inhibitor Mycludex B Objective:
The objective of the clinical trial is the evaluation of safety and tolerability, as well as efficacy of Myrcludex B in patients with primary biliary cirrhosis.

| | Protocol Number: MYR 205 |
|---|---|
| | Study drug: Myrcludex B (MXB) |
| Study title | Am multi-center, randomized, multi-dose, parallel arm trial to evaluate safety and efficacy of MXB in combination with UDCA (the current standard of care) in patients with proven or likely diagnosis of primary billiary cirrhosis (PBC). |
| Clinical phase | 2 |
| Number of patients | 120, randomized 1:1:1:1 in 4 treatment arms |
| Study design | Arm 1: MXB 2 mg + UDCA 12 weeks |
| | Arm 1: MXB 5 mg + UDCA 12 weeks |
| | Arm 1: MXB 10 mg + UDCA 12 weeks |
| | Arm 1: UDCA 12 weeks |
| | Visits: |
| | SCR, BL, week 2, week 4, week 8, week 12 (EoT), week 14 (EoFU) |
| | Evaluations: physical, vital signs, ECG (SCR, EoT), AEs, Fibroscan (SCR, EoT), clinical chemistry, hematology, blood bile acids, liver panel, FGF-19 levels, urinalysis, SF-36 QOL questionnaier, Pruritis VAS questionnair. |
| Endpoints | Primary |
| | Percent change (%) in serum ALP from Baseline to End of Study (EOS) [EOS = Day 85 or last observed ALP value on treatment]. |
| | Secondary |
| | 1. Absolute and percent changes in serum ALP levels from Baseline to Day 15, Day 29, Day 57, Day 85/ET and Follow-Up (Day 99) |

Protocol Number: MYR 205
Study drug: Myrcludex B (MXB)

|  |  |  |
|---|---|---|
|  | 2. | Absolute and percent change in serum gamma-glutamyl transferase (GGT), alanine aminotransferase (ALT), and aspartate aminotransferase (AST) values from Baseline to Day 15, Day 29, Day 57, Day 85/ET and Follow-Up (Day 99) |
|  | 3. | Absolute and percent changes in serum albumin and conjugated (direct) bilirubin values from Baseline to Day 15, Day 29, Day 57, Day 85/ET and Follow-Up (Day 99) |
|  | 4. | Enhanced liver fibrosis (ELF) score and change in levels of its components, hyaluronic acid, aminoterminal peptide of pro-collagen III, and tissue inhibitor of matrix metalloproteinase-1 from Baseline to Day 85/ET |
|  | 5. | Absolute and percent changes in levels of C-reactive protein, non-esterified fatty acid, tumor necrosis factor alpha, tumor necrosis factor beta, tumor growth factor beta, bile acids, glutathione, immunoglobulin M, and osteopontin from Baseline to Day 85/ET |
|  | 6. | Disease-specific and general health questionnaires: |
|  | a. | SF-36 Quality of Life Questionnaire (QOL): Change from Baseline to Day 85/ET for scale scores and summary measures |
|  | b. | PBC-40 QOL Questionnaire: Change from Baseline to Day 29, Day 57, and Day 85/ET for each of 5 domains |
|  | c. | Bile acid analysis: Absolute and percent changes in the levels of total bile acids from Baseline to Day 85/ET |
|  | 7. | Absolute and percent change in fibroblast growth factor-19 (FGF-19) levels from Baseline to Day 85/ET |
| Main inclusion criteria | 1. | Adult male or female and on a stable dose of UDCA for at least 6 months prior to screening |
|  | 2. | Screening ALP level between 1.5x upper limit of normal (ULN) and 10 × ULN |
|  | 4. | Proven or likely PBC, as demonstrated by the patient presenting with at least 2 of the following 3 diagnostic factors: |
|  | a. | History of increased ALP levels for at least 6 months prior to Day 0 |
|  | b. | Positive antimitochondrial antibody (AMA) titer |
|  | c. | Liver biopsy consistent with PBC |
| Main exclusion criteria | 1. | History or presence of other concomitant liver diseases, for example, hepatitis B or C, primary sclerosing cholangitis, alcoholic liver disease, definite autoimmune liver disease, or biopsy proven nonalcoholic steatohepatitis |
|  | 2. | History or presence of hepatic decompensation (e.g., variceal bleeds, encephalopathy, or poorly controlled ascites) |
|  | 3. | Screening conjugated (direct) bilirubin >2x ULN; ALT or AST >5 × ULN; serum creatinine >1.5 mg/dL (133 μmol/L) |
|  | 4. | History or presence of other concomitant liver diseases or human immunodeficiency virus (HIV) or other viral hepatitis infection |
|  | 5. | Clinically significant medical condition |
|  | 6. | Participation in another investigational drug, biologic, or medical device study within 30 days prior to Day 0 |
|  | 7. | If female: pregnant, lactating, or positive serum or urine pregnancy test |
|  | 8. | On concomitant medications including colchicine, methotrexate, azathioprine, or systemic corticosteroids (during the 3 months prior to enrollment) |

BIBLIOGRAPHY

Shih, D. M., Shaposhnik, Z., Meng, Y., Rosales, M., Wang, X., Wu, J., . . . Lusis, A. J. (2013). Hyodeoxycholic acid improves HDL function and inhibits atherosclerotic lesion formation in LDLR-knockout mice. FASEB Journal, 27(9), 3805-3817. http://doi.org/10.1096/fj.12-223008

Talwalkar, J. A., & Lindor, K. D. (2003). Primary biliary cirrhosis. Lancet, 362(9377), 53-61. http://doi.org/S0140-6736(03)13808-1 [pii]\r10.1016/S0140-6736(03)13808-1

Davis, B. K., Wen, H., and Ting, J. P. (2011). The inflammasome NLRs in immunity, inflammation, and associated diseases. Annu. Rev. Immunol. 29, 707-735 Martinon, F., Petrilli, V., Mayor, A., Tardivel, A., and Tschopp, J. (2006). Gout-associated uric acid crystals activate the NALP3 inflammasome. Nature 440, 237-241

Schroder, K., Zhou, R., and Tschopp, J. (2010). The NLRP3 inflammasome: a sensor for metabolic danger? Science 327, 296-300

Miller L C et al, (1995) Synthesis of interleukin-1β in primary biliary cirrhosis: Relationship to treatment with methotrexate or colchicine and disease progression Hepatology Volume 22, Issue 2, 518-524

The invention claimed is:

1. A method for treatment of primary biliary cirrhosis in a subject in need thereof comprising administering an effective amount of a Na+-taurocholate cotransporting polypeptide (NTCP) inhibitor to the subject,
   wherein the NTCP inhibitor is a pre-S1 peptide inhibitor,
   wherein the pre-S1 peptide inhibitor comprises a peptide comprising amino acid sequence NPLGFX$_0$P (SEQ ID NO: 15), and
   wherein X$_0$ is any amino acid.

2. The method of claim 1, wherein X$_0$ is F or L.

3. The method of claim 1, wherein the pre-S1 peptide inhibitor further comprises an N-terminal sequence of at least 4 amino acids at the N-terminus of NPLGFX$_0$P (SEQ ID NO: 15).

4. The method of claim 1, wherein the pre-S1 peptide inhibitor further comprises a C-terminal sequence of at least 1 amino acid at the C-terminus of NPLGFX$_0$P (SEQ ID NO: 15).

5. The method of claim 1, wherein of the pre-S1 peptide inhibitor comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids.

6. The method of claim 1, wherein the pre-S1 peptide inhibitor comprises a pre-S1 peptide of an HBV virus, or a functional fragment thereof, wherein the function is binding to NTCP, inhibition of NTCP, or reduction of NTCP activity, wherein the pre-S1 peptide inhibitor comprises or consists of:

at least amino acids 9 to 15, 8 to 15, 7 to 15, 6 to 15, 5 to 15, 4 to 15, 3 to 15, 2 to 15 of a pre-S1 peptide of an HBV virus;

at least amino acids 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 9 to 31, 9 to 32, 9 to 33, 9 to 34, 9 to 35, 9 to 36, 9 to 37, 9 to 38, 9 to 39, 9 to 40, 9 to 41, 9 to 42, 9 to 43, 9 to 44, 9 to 45, 9 to 46, 9 to 47, 9 to 48 of a pre-S1 peptide of an HBV virus;

at least amino acids 8 to 16, 7 to 17, 6 to 18, 5 to 19, 4 to 20, 3 to 21, or 2 to 22 of a pre-S1 peptide of an HBV virus;

at least amino acids 2 to 15, 2 to 16, 2 to 17, 2 to 18, 2 to 19, 2 to 19, 2 to 20, 2 to 21, 2 to 22, 2 to 23, 2 to 24, 2 to 252 to 26, 2 to 27, 2 to 28, 2 to 29, 2 to 30, 2 to 31, 2 to 32, 2 to 33, 2 to 34, 2 to 35, 2 to 36, 2 to 37, 2 to 38, 2 to 39, 2 to 40, 2 to 41, 2 to 42, 2 to 43, 2 to 44, 2 to 45, 2 to 46, 2 to 47, or 2 to 48 of a pre-S1 peptide of an HBV virus;

at least amino acids 9 to 15 and 16 to 20 of a pre-S1 peptide of an HBV virus;

at least amino acids 2 to 8 and 9 to 15 of a pre-S1 peptide of an HBV virus;

at least amino acids 2 to 8, 9 to 15 and 16 to 20 of a pre-S1 peptide of an HBV virus;

at least amino acids 9 to 15 and 34 to 48 of a pre-S1 peptide of an HBV virus;

at least amino acids 9 to 15, 16 to 20 and 34 to 48 of a pre-S1 peptide of an HBV virus;

at least amino acids 2 to 8, 9 to 15 and 34 to 48 of a pre-S1 peptide of an HBV virus;

at least amino acids 2 to 8, 9 to 15, 16 to 20 and 34 to 48 of a pre-S1 peptide of an HBV virus;

at least amino acids 2 to 48 of a pre-S1 peptide of an HBV virus or a portion thereof of at least 15 amino acids;

amino acids 2 to 48 of a pre-S1 peptide of an HBV virus; or a sequence having at least 50%, 55%, 60%, 65%, 70%, 75%, 80%, 85%, 90%, or 95% identity with any of the above sequences.

7. The method of claim 6, wherein the HBV virus is HBV strain alphal, HBV strain LSH, woodchuck HBV, Woolly Monkey HBV (WMHBV), orangutan HBV, chimpanzee HBV, gorilla HBV, human HBV, HBV subtype AD, ADR, ADW, ADYW, AR or AYW, or HBV genotype A, B, C, D, E, F, G or H.

8. The method of claim 1, wherein the pre-S1 peptide inhibitor comprises of amino acid sequence

```
                                           (SEQ ID NO: 1)
(-11)-M GGWSS TPRKG MGTNL SVPNP LGFFP DHQLD PAFRA
NSNNP DWDFN PNKDH WPEAN KVG-48

(SEQ ID NO: 2)
(-11)-M GGWSS KPRKG MGTNL SVPNP LGFFP DHQLD PAFGA
NSNNP DWDFN PVKDD WPAAN QVG-48

(SEQ ID NO: 3)
(-11)-M GGWSS KPRKG MGTNL SVPNP LGFFP DHQLD PAFKA
NSENP DWDLN PHKDN WPDAN KVG-48

(SEQ ID NO: 4)
(-11)-M GGWSS KPRQG MGTNL SVPNP LGFFP DHQLD PAFGA
NSNNP DWDFN PNKDH WPEAN QVG-48

(SEQ ID NO: 5)
1-MGQNL STSNP LGFFP DHQLD PAFRA NTANP DWDFN PNKDT
WPDAN KVG-48

SEQ ID NO: 6)
(-10)-MGLSW TVPLE WGKNI STTNP LGFFP DHQLD PAFRA
NTRNP DWDHN PNKDH WTEAN KVG-48

(SEQ ID NO: 7)
(-11)-M GAPLS TTRRG MGQNL SVPNP LGFFP DHQLD PLFRA
NSSSP DWDFN TNKDS WPMAN KVG-48

(SEQ ID NO: 8)
(-10)-MGLSW TVPLE WGKNL SASNP LGFLP DHQLD PAFRA
NTNNP DWDFN PKKDP WPEAN KVG-48

(SEQ ID NO: 9)
(-11)-M GAPLS TARRG MGQNL SVPNP LGFFP DHQLD PLFRA
NSSSP DWDFN TNKDN WPMAN KVG-48

(SEQ ID NO: 10)
1-MGLNQ STFNP LGFFP SHQLD PLFKA NAGSA DWDKN PNKDP
WPQAH DTA
```

```
                                          (SEQ ID NO: 11)
(-11)-M GGWSS KPRQG MGTNL SVPNP LGFFP DHQLD PAFGA
NSNNP DWDFN PNKDH WPEAN KVG-48,
``` or a fragment thereof of at least 15 amino acids, or a sequence having at least 50%, 55%, 60%, 65%, 70%, 75%, 80%, 85%, 90%, or 95% identity with any of the above sequences, wherein the pre-S1 peptide inhibitor comprises amino acid sequence

```
                                          (SEQ ID NO: 12)
GTNL SVPNP LGFFP DHQLD PAFRA NSNNP DWDFN PNKDH
WPEAN KVG;

(SEQ ID NO: 13)
GTNL SVPNP LGFFP DHQLD PAFGA NSNNP DWDFN PNKDH
WPEAN KVG;

(SEQ ID NO: 14)
GTNL SVPNP LGFFP DHQLD PAFGA NSNNP DWDFN PNKDH
WPEAN QVG;
``` or a sequence having at least 50%, 55%, 60%, 65%, 70%, 75%, 80%, 85%, 90%, or 95% identity with any of the above sequences.

9. The method of claim 1, wherein the pre-S1 peptide inhibitor is modified by at least one hydrophobic moiety at the N-terminus or in 1, 2, 3, or 4 amino acids proximity to the N-terminus.

10. The method of claim 1, wherein the pre-S1 peptide inhibitor is Myristoyl-

```
                                          (SEQ ID NO: 13)
GTNLSVPNPLGFFPDHQLDPAFGANSNNPDWDFNPNKDHWPEA
NKVG-amide.
```

11. The method of claim 1, wherein the method comprises administering the pre-S1 inhibitor and a further NTCP inhibitor.

12. The method of claim 1, wherein the subject is a human.

13. The method of claim 1, wherein the method results in the reduction, or elimination of symptoms of primary biliary cirrhosis.

14. The method of claim 3, wherein the N-terminal sequence comprises amino acid sequence $NX_1SX_2X_3$ (SEQ ID NO: 16), wherein each of $X_1$, $X_2$ and $X_3$ is any amino acid.

15. The method of claim 14, wherein $X_1$ is L, I or Q; $X_2$ is T, V, A or is absent; and $X_3$ of is P, S, T or F.

16. The method of claim 4, wherein the C-terminal sequence comprises amino acid sequence $X_4HQLDP$ (SEQ ID NO: 18), wherein $X_4$ is any amino acid.

17. The method of claim 16, wherein X4 is D, E or S.

18. The method of claim 9, wherein the hydrophobic moiety modification is acylation.

\* \* \* \* \*